US006228842B1

(12) United States Patent
Fronko et al.

(10) Patent No.: US 6,228,842 B1
(45) Date of Patent: May 8, 2001

(54) **PACIDAMYCINS PRODUCED BY *STREPTOMYCES COERULEORUBIDUS***

(75) Inventors: Richard Fronko, Milpitas; May Lee; Ving J. Lee, both of Los Altos; Roger Leger, Mountain View, all of CA (US)

(73) Assignee: Microcide Pharmaceuticals, Inc., Mountain View, CA (US)

( * ) Notice: Subject to any disclaimer, the term of this patent is extended or adjusted under 35 U.S.C. 154(b) by 0 days.

(21) Appl. No.: 09/188,057

(22) Filed: Nov. 6, 1998

(51) Int. Cl.$^7$ .......................... A61K 38/05; A01N 43/48; C12P 21/02; C12N 1/20
(52) U.S. Cl. ................ 514/19; 514/50; 435/71.3; 435/252.35
(58) Field of Search ..................... 536/1.11, 4.1, 536/6.2; 514/2, 8, 23, 19, 50; 530/335, 345, 300; 435/254.1, 252.35, 71.3

(56) References Cited

U.S. PATENT DOCUMENTS

| | | | |
|---|---|---|---|
| 4,180,564 | 12/1979 | Godfrey et al. | 424/117 |
| 4,499,075 | 2/1985 | Lee et al. | 424/118 |
| 4,677,071 | 6/1987 | Lee et al. | 435/253.5 |
| 5,039,663 | 8/1991 | Haneishi et al. | 514/18 |
| 5,041,423 | 8/1991 | Haneishi et al. | 514/18 |
| 5,213,974 | 5/1993 | Haneishi et al. | 435/118 |

FOREIGN PATENT DOCUMENTS

| | | |
|---|---|---|
| 0 005 956 A1 | 12/1979 | (EP) . |
| 0 487 756 A1 | 6/1992 | (EP) . |
| 846801 | 8/1960 | (GB) . |

OTHER PUBLICATIONS

Rudinger, J. In "Peptide Hormones," Parsons, J.A., Editor, (1976) (University Park Press: Baltimore MD) p. 1–7, Jun. 1976.*
Chen et al. J. Antibiotics (1989) 42(4): 512–520, Apr. 1989.*
Chatterjee et al., "Napsamycins, New Pseudomonas Active Antibiotics of the Mureidomycin Family From Streptomyces sp. HIL Y–82, 11372," *J. of Antibiotics* 47:595–598 (1994).
Inukai et al., "Mureidomycins A–D, Novel Peptidylnucleoside Antibiotics With Spheroplast Forming Activity," *J. of Antibiotics* 42:662–679 (1989).
Karwowski et al., "Pacidamycins, a Novel Series of Antibiotics With Anti–*Pseudomonas aeruginosa* Activity," *J. of Antibiotics* 42:506–511 (1989).

* cited by examiner

*Primary Examiner*—Jon P. Weber
*Assistant Examiner*—Michael V. Meller
(74) *Attorney, Agent, or Firm*—Lyon & Lyon LLP

(57) ABSTRACT

The invention provides novel antibiotics of the pacidamycin group of uridyl peptide antibiotics and methods of preparing and using those compounds.

15 Claims, 21 Drawing Sheets

Pacidamycin-D

Pacidamycin-4N

FIGURE 15 Pacidamycin-5N

Pacidamycin-5T

CUPA

PACIDAMYCINS PRODUCED BY STREPTOMYCES COERULEORUBIDUS

BACKGROUND OF THE INVENTION

This invention relates to the field of treatment of bacterial infections, and, in particular, to new pacidamycins.

The following description of the background of the invention is provided solely to aid in understanding the present invention. None of the references cited are admitted to be prior art to the present invention.

A number of different antibiotics with certain structural similarities to the compounds of this invention have been identified in publications and patents. These include the pacidamycins described by J. P. Karwowski et al, in *Journal of Antibiotics*, 42:506–526, 1989. The mureidomycins described in U.S. Pat. No. 5,039,663 (Aug. 13, 1991) and by M. Inukai et al, in *Journal of Antibiotics*, Vol. 42:662–679, 1989 are related compounds containing a methionine moiety. Napsamycins, as described, for example, in European Patent Application publication number 0 487 756 A1 (Mar. 6, 1992) and by S. Chatterjee et al., in *Journal of Antibiotics*, 47:595–598, 1994, are mureidomycins with a modified N-terminus. Additional related compounds are described in U.S. Pat. No. 4,180,564 (Dec. 25, 1979) and U.S. Pat. No. 4,499,075 (Feb. 2, 1985). These compounds, while not fully characterized, appear to be related to the mureidomycins or the pacidamycins based on their physical-chemical properties, chemical degradation products and biological properties.

All of the above references are incorporated herein by reference in their entireties, including any drawings.

SUMMARY OF THE INVENTION

The present invention concerns the identification of new pacidamycins and derivatives. These compounds were isolated from fermentation broths of *Streptomyces coeruleorubidus* NRRL 18730. Thus, the present invention concerns the new antibiotic compounds and derivatives of those and other uridyl peptide antibiotics compounds, methods of preparing those compounds, and the use of those compounds and compositions including those compounds to inhibit microbial growth, preferably bacterial growth or fungal growth.

Thus, in a first aspect, this invention provides enriched, isolated or purified antibiotic compounds identified herein as pacidamycin-D, pacidamycin-4N, pacidamycin-5N, and pacidamycin-5T, and derivatives of these compounds. This includes enriched preparations, such as those obtained by partial purification from fermentations of *Streptomyces coeruleorubidus*, NRRL 18730 or other strain producing one or more of these compounds.

The term "uridyl peptide antibiotic" refers to a compound having antibacterial and/or antifungal activity which includes a plurality of amino acid residues, preferably with 4, 5,or 6 amino acid residues, where the C-terminal amino acid is linked to the rest of the molecule through a urea group. The molecule has a uridine or uridine derivative group attached to one of the amino acid residues, preferably through a ribose=C—NHC(O)— linkage. A uridine derivative group may be substituted or modified on the sugar or on the base, for example, by the addition or removal of one or more hydroxyl groups. For example, the group may include a dihydrouracil group.

The terms "pacidamycin", "mureidomycin", and "napsamycin" refer to groups of uridyl peptide antibiotics as described in references cited herein. The "mureidomycins" are uridyl peptide antibiotics having a methionine residue linked to the urea group which is linked to the C-terminal amino acid. The "pacidamycins" are uridyl peptide antibiotics having an alanine residue linked to the urea group which is linked to the C-terminal amino acid. The "napsamycins" are similar to the mureidomycins, except they possess a substituted 1,2,3,4-tetrahydroisoquinoline-3-carboxylic acid residue as the N-terminal amino acid.

Pacidamycin-D, pacidamycin-4N, pacidamycin-5N, and pacidamycin-5T are characterized and defined by the purification and physical and spectroscopic properties described below. The structures assigned are based on the physical and spectroscopic data, and are believed to be correct. However, in the event that the structural assignments are not fully correct, one skilled in the art will recognize that the compounds are fully identified by the purification and physical and spectroscopic data.

In connection with the compounds of this invention, the term "derivative" refers to compounds which retain the characteristic core structure of the corresponding base compound except that the C-terminal amino acid may be removed, modified, or replaced with another desired group, for example, a different amino acid. In particular, the term "derivative" includes the examples described by the generic description of compounds which may be derived from the CUPA compounds as described below.

In another aspect, the invention provides a uridyl peptide antibiotic derivative, e.g., a pacidamycin derivative, which has the carboxy terminal amino acid, modified, removed, or replaced with a different moiety. The compound resulting from removal of the C-terminal amino acid residue is termed a CUPA compound, for example, as shown in FIG. 21, or a corresponding molecule prepared by removal of the C-terminal amino acid from a different uridyl peptide antibiotic compound, preferably from a pacidamycin, more preferably from pacidamycin 1,4,5,6,D,4N,5N, or 5T, most preferably from pacidamycin D, 4N, 5N, or 5T. However, CUPA molecules can also be prepared from mureidomycins or napsamycins or other uridyl peptide antibiotic compounds. In general, the urea carbonyl through which the C-terminal amino acid is attached to the remainder to the molecule is preferably also removed. Such decarbonylation can be performed by standard methods.

In the context of CUPA compounds, the term "modification" in reference to the C-terminal amino acid means the attachment, removal, or alteration of one or more substituent groups on the C-terminal amino acid residue. Preferably this is performed by the removal of the original terminal amino acid and replacement with a modified form of the amino acid. In connection with the C-terminal amino acid modifications, the term "removal" refers to the cleavage of degradation of the C-terminal acid from the remainder to the molecule, and can also include the removal of the urea linkage carbonyl group. Also in connection with the C-terminal amino acid modifications, the term "replacement" refers to the attachment of a substituent group or moiety through the same atom as for the original C-terminal amino acid residue. Preferably the replacement group or moiety is also through a urea linkage, particularly where the replacement group or moiety is a different or modified amino acid. Thus, CUPA compounds can be used to provide additional derivatives of uridyl peptide antibiotic compounds.

In a related aspect, this invention provides pharmaceutical compositions which include pacidamycin-D, pacidamycin-4N, pacidamycin-5N, pacidamycin-5T, a CUPA compound, or derivatives of these compounds, preferably with a pharmaceutically acceptable carrier or excipient.

In another related aspect, this invention provides methods of using the above compounds to inhibit the growth of a microorganism, preferably a bacterium or a fungus. Such methods involves contacting such a microbe with at least one of the compounds pacidamycin-D, pacidamycin-4N, pacidamycin-5N, pacidamycin-5T, a CUPA compound, or derivatives of these compounds. The compound or compounds can be provided in the form of a pharmaceutical composition. The compound should preferably be provided such that the microorganism is contacted at a concentration above the MIC of the microorganism for the particular compound.

In another related aspect, the invention provides a method to treat an infection of an animal, preferably a mammal, by a microorganism, for example, by a bacterium or a fungus. The method involves administering to an animal suffering from such an infection a therapeutically effective amount of pacidamycin-D, pacidamycin-4N, pacidamycin-5N, pacidamycin-5T, a CUPA compound, or derivatives of these compounds.

Similarly, in a related aspect, the invention provides a prophylactic treatment method, in which a therapeutically effective amount of pacidamycin-D, pacidamycin-4N, pacidamycin-5N, pacidamycin-5T, a CUPA compound, or derivatives of these compounds is administered to an animal at risk of an infection by a microorganism, preferably a bacterium or a fungus. Preferably the animal is a mammal, more preferably a human. The compound or compounds may be provided in the form of a pharmaceutical composition.

Similarly, the invention provides methods for treating or preventing infections of plants by administering at least one compound of the present invention or a composition containing such a compound. Such a composition includes at least one other compatible component, for example, a carrier, diluent, additional active compound, protectant, or other compound selected to facilitate administration or preserve or enhance activity of the composition.

In aspects and embodiments involving inhibition of a microorganism or prophylactic or therapeutic treatment of an infection involving or potentially involving such a microorganism the microorganism is preferably a bacterium, such as a Staphylococcal, Enterococcal, Pseudomonal, or Mycobacterial organism or an Enterobacteriaceae, or is a fungus, such as an Aspergillus species (e.g., *A. nidulans, A. fumigatus*), or Candida species (e.g., *C. lipolytica, C. fropicalis, C. neoformans, C. albicans, C. glabrala, C. krusei*). In further embodiments, the organism is from a genus or species as identified herein.

Also provided are methods for preparing pacidamycin-D, pacidamycin-4N, pacidamycin-5N, or pacidamycin-5T, and derivatives of these compounds. The method involves separating one or more of the above compounds from other uridyl peptide antibiotic compounds produced by an organism. Generally the method will include growing (e.g., a fermentation) a culture of Streptomyces strain which produces one or more of the above compounds under conditions such that one or more of the above compounds is excreted into the culture medium, and isolating, enriching or purifying the desired compound from the culture medium. Preferably the Streptomyces strain is a *Streptomyces coeruleorubidus* strain, most preferably *Streptomyces coeruleorubidus*, NRRL 18730. The process of isolating, enriching or purifying can involves steps such as those described in the Detailed Description below, for example, separation of liquid medium from solid materials, precipitation, ion exchange chromatography and other chromatographic methods. The method preferably includes one or more ion exchange chromatography steps to separate the pacidamycin-D, pacidamycin-4N, pacidamycin-5N, and/or pacidamycin-5T from other pacidamycins or uridyl peptide antibiotics produced by the organism. The method also may include a further reverse phase chromatography step or other separation to separate the new pacidamycins of the present invention from each other and/or from remaining other pacidamycins or other uridyl peptide antibiotics, for example, as described in the Examples below.

Also provided is a method for the preparation of new uridyl peptide antibiotics from the natural products (e.g., pacidamycins, mureidomycins, and napsamycins). Site-specific degradation of either a purified natural product or a complex of antibiotics with a peptidase (i.e., carboxypeptidase) affords a truncated structure (which may have antimicrobial, e.g., antibacterial or antifungal activity), referred to generically as CUPA. The method involves removal of the carboxy terminus amino acid of a uridyl peptide antibiotic, preferably of a pacidamycin, most preferably of any of pacidamycins 1,4,5,6,4N,5N,5T, or D. The CUPA intermediate may also be derivatized through replacement of the original C-terminal amino acid with a different amino acid or other substituent. Preferably, the method involves digestion of a uridyl peptide antibiotic, for example, a pacidamycin, a mureidomycin, or a napsamycin, with a carboxy-selective peptidase more preferably carboxypeptidase A. Removal of the C-terminal amino acid affords a transient carbamic acid which undergoes spontaneous decarboxylation (e.g., the ureido carbonyl). The CUPA preferably retains antibacterial activity. However, even without retention of activity, a CUPA intermediate can be used to construct new uridyl peptide antibiotics which have antibacterial activity.

While the pacidamycins are exemplified, other similar natural products (e.g., mureidomycins or napsamycins) are also suitable starting materials for carboxypeptidase A degradation. These CUPA intermediates on modification will provide new mureidomycins and napsamycins.

The CUPA intermediates are then refunctionalized with activated α-isocyanato acids or synthetic equivalents (Scheme 1), or with isocyanates (Scheme 2) to afford new structural entities. Examples of α-isocyanato acid equivalents are shown below where X is any suitable leaving group. While this list is not comprehensive, it provides those skilled in the art an appreciation of the scope of the chemistry. The selection of protecting groups $R^4$ is not limited to those listed, but serves to illustrate the breadth of structures that are compatible with the process. The term "[]synthetic equivalents" means chemical entities or reactants that will append the desired substituent(s) as shown below.

Scheme 1

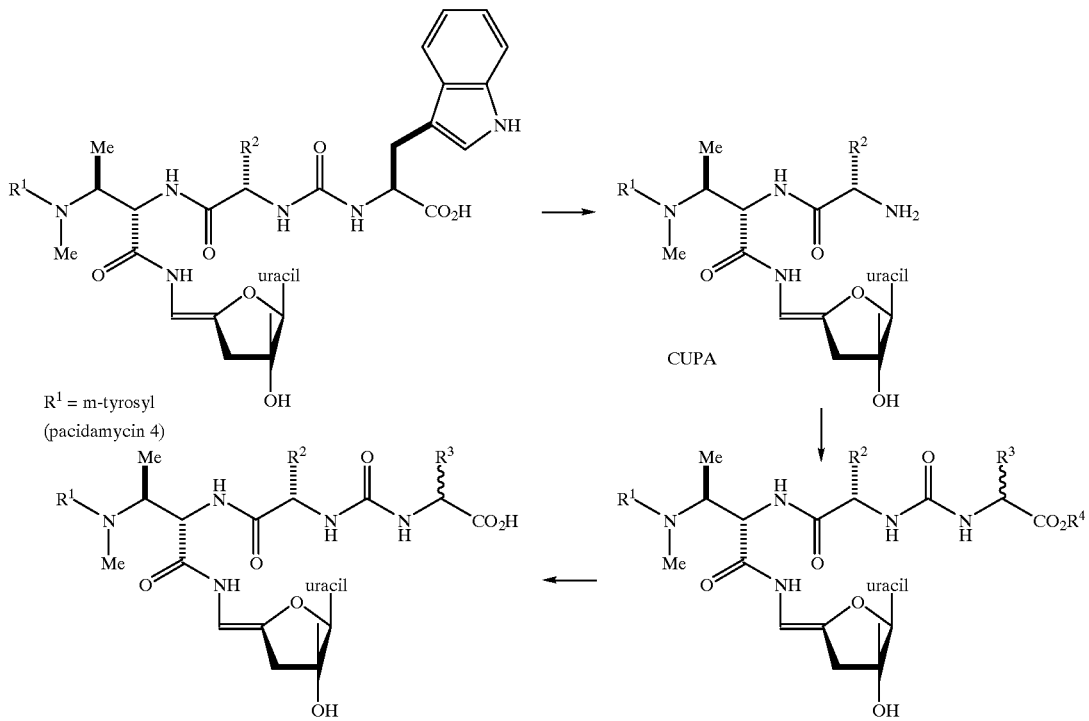

R[1] = m-tyrosyl
(pacidamycin 4)

R[1] = alanyl, m-tyrosyl alanyl-m-tyrosyl; glycyl-m-tyrosyl, 1,2,3,4-tetrahydroisoquinoline-3-carboxyl

R[2] = $CH_3$, $CH_2CH_2SCH_3$

R[3] = H, $C_n$-alkyl, $-(CH_2)_nNH_2$, $-(CH_2)_nNH(C=NH)NH_2$, $(CH_2)_nCOOH$ $CH_2SH$, $CH_2OH$, $CH_2CH_2SCH_3$, benzyl, indole-3-methyl, 4-halobenzyl (halo=bromo, chloro, fluoro, or iodo), 4-(or 3)-hydroxybenzyl, thienyl-3-methyl; n=1–4

R[4] = $C_n$-alkyl, benzyl, p-methoxybenzyl, p-nitrobenzyl, trityl, 4-methoxytrityl, trimethylsilyl, phenyldimethylsilyl, t-butyldimethylsilyl, $CH_2OCH_3$, tetrahydropyranyl, $C(CH_3)_2OCH_3$, $CH_2CCl_3$

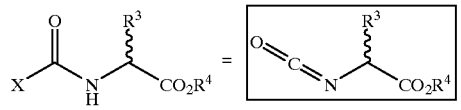

X = Cl, $4\text{-}NO_2C_6H_4CH_2O$, $2,4\text{-}(NO)_2C_6H_3CH_2O$, $C_6F_5O$, $C_6Cl_5O$, $C_6F_5S$, $(C_1\text{--}C_4)$-alkylS, imidazolyl, pyrrolyl, pyrazolyl Scheme 2

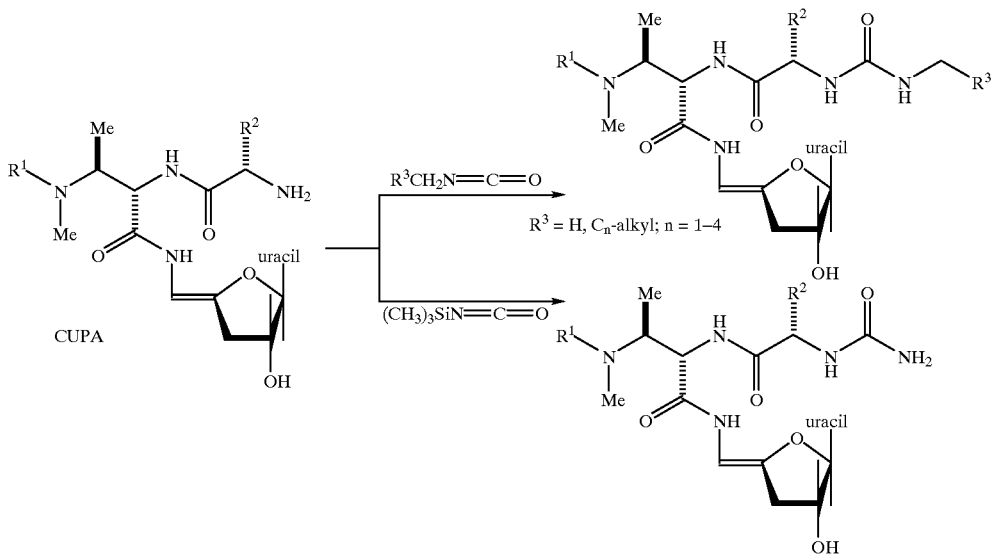

As indicated above, in preferred embodiments it is advantageous for the compounds of this invention to be "enriched". In this context, the term "enriched" means that the compound of interest is present as a larger percentage of a mixture of bioactive compounds having antimicrobial (preferably antibacterial or antifungal) activity, e.g., uridyl peptide antibiotic compounds, than in a natural growth medium of an organism producing the compound. Thus, preferably a fraction containing the present pacidamycin fraction has been increased at least 2-fold, more preferably at least 5- or 10-fold, still more preferably at least 100-fold, and most preferably at least 1000-fold with respect to other pacidamycins and/or other uridyl peptide antibiotics, e.g., napsamycins and mureidomycins. Thus, as applied to one or more of the novel pacidamycins described herein, in the case of organisms which produce one or more previously described uridyl peptide antibiotics in addition to one or more of the novel pacidamycins of this invention, the term "enriched" means that one or more of the novel pacidamycins identified herein is present in a mixture of active compounds as a greater proportion relative to the previously described uridyl peptide antibiotics than occurs in the growth medium or in the steps of the purification processes described in the corresponding patent or other publication.

Similarly, the term "isolated" indicates that the compound of interest has been separated from at least some of the compounds with which it is normally found. Thus, for the pacidamycins described herein, "isolated" typically means that the compound of interest has been separated from at least some of the components naturally present in a medium in which the compound has been produced by an organism. Preferably the compound of interest has been separated from at least 10% or 20% of the compounds with which it naturally occurred, more preferably from at least 40% or 50%, still more preferably from at least 70% or 80%, and most preferably from at least 90%, 95%, or 99% of the compounds with which it naturally occurs. In the case of isolation of one or more of the present novel pacidamycins from an organism which also produces one or more previously described uridyl peptide antibiotics, the term "isolated" means that at least one of the present compounds has been separated from at least a fractional portion of the previously described uridyl peptide (e.g., previously described pacidamycin, napsamycin, or mureidomycin), preferably from percentages as indicated above.

The term "purified" in this context means that a particular compound of this invention constitutes a greater proportion of the uridyl peptide antibiotic compounds present in a composition than in a naturally occurring composition, as compared to any other of the uridyl peptide antibiotics in the composition, for example, any other pacidamycin, napsamycin, or mureidomycin in the composition. It does not mean that no other compounds may be present. Preferably, "purified" indicates that the proportion of the present compound present in a mixture is at least 2-fold, more preferably at least 5-fold or 10-fold, still more preferably at least 100-fold, and most preferably at least 1000-fold greater than in the culture medium of an organism naturally producing that compound and, in particular, the fold increase is relative to previously described uridyl peptide antibiotics co-produced by an organism, including other of the new pacidamycins described herein.

The term "therapeutically effective amount" refers to an amount which is sufficient to provide a therapeutic effect. A "therapeutic effect" is one which at least partially alleviates at least one symptom or condition. Thus, for example, in connection with a bacterial infection a "therapeutic effect" relieves, to some extent, one or more of the symptoms of the infection, and can involve a reduction in the rate of growth of bacteria involved in the infection, which can include curing an infection. Curing means that the symptoms of active infection are eliminated, including the elimination of excessive numbers of viable bacteria of those involved in the infection. However, certain long-term or permanent effects of the infection may exist even after a cure is obtained (such as extensive tissue damage).

Similarly, in connection with prophylactic methods, the term "prophylactically effective amount" means an amount sufficient to prevent the establishment of a clinically significant population of an organism, e.g., a bacterium, susceptible to a relevant therapeutic compound, e.g., an antibiotic, in a treated animal. Thus, the amount is sufficient to prevent establishment of an infection which will require treatment of the infection. For organisms, e.g. bacteria, which are not part of the normal flora of an animal, the amount of the compound is preferably sufficient to prevent the establishment of any population of the organism.

In connection with a microbial infection, e.g., a bacterial infection, the term "suffering" indicates that an individual has an active population of the microbe which is higher than normal or higher than is compatible with health. Usually, but not necessarily, the population is at a level such that one or more deleterious symptoms in the individual result. However, an infection may be at a non-symptomatic level but may pose a risk of further development of infection sufficient to justify medical intervention or may be pre-symptomatic such that symptoms may be expected to develop if the infection is allowed to continue without treatment for a longer period of time.

The term "microbe" is used in its usual biological sense to refer to very small organisms, which generally are only readily observable when viewed under a microscope or when aggregated. Thus, the organism is generally of less than 1 mm in average dimension, more typically less than 100 $\mu$m, and often less than 10 $\mu$m. However, it is understood that certain microbes have such size only during certain stages of the life cycle. The term "microbe" is also meant to include fungi which have a mycelial vegetative stage. In this case, the term "microbial cell" can refer to a coenocytic or mycelial structure, which is generally polynucleate. Thus, the term "microbe" includes, for example, bacteria, algae, fungi, and protozoans.

The terms "fungus" and "fungi" refer to lower eukaryotic organisms as generally understood by those skilled in the art. Commonly fungi have a mycelial or coenocytic vegetative stage. However, in the context of this invention, unless specifically indicated to the contrary, included are the yeasts (e.g., Saccharomyces species). In this context, "yeast" refers to a lower eukaryotic organism which has a single-celled growth stage and is classified within the fungi, for example, based on properties such as cell structure, reproductive mechanisms, nucleic acid sequence comparisons or other characteristics commonly utilized for classifying organisms. The fungi include the following classes: Zygomycetes, Ascomycetes, the Basidiomycetes, Deuteromycetes, and Oomycetes.

The terms "bacteria", "bacterium", and "bacterial" are used in their usual senses to refer to prokaryotic organisms. The term "bacterium" includes both single cell and a plurality or population of cells of a particular prokaryotic organism unless clearly indicated to the contrary.

The terms "Staphylococcal", "Enterococcal", "Pseudomonal", and "Mycobacterial" are used as commonly understood in the art to refer to an organism or organisms which are identified as belonging to the bacterial genus classifications of Staphylococcus (e.g., *S. aureus*), Enterococcus (e.g., *E. faecalis* and *E. faecium*), Pseudomonas (e.g., *P. aeruginosa*), and Mycobacterium (e.g., *M tuberculosis*) respectively. The term "an Enterobacteriaceae" refers to an organism with that family, including, for example, an organism which falls within the genera Citrobacter (e.g., *C. freundii*), Enterobacter (e.g., *E. cloacae* and *E. aerogenes*), Escherichia (e.g., *E. coli*), Klebsiella (e.g., *K. pneumoniae* and *K. oxytoca*), Morganella (e.g., *M. morganii*), Proteus (e.g., *P. mirabilis, P. vulgaris*), Providencia (e.g., *P. alcalifaciens, P. rettgeri, P. stuartii*), Salmonella (e.g., *S. typhimurium, S. typhi, S. paratyphi, S. enteritidis*), Serratia (e.g., *S. marcescens*), Shigella (e.g., *S. dysenteriae, S. flexneri, S. sonnei*), and Yersinia (e.g., *Y. enterocolitica, Y. pseudotuberculosis, Y. intermedia, Y. pestis*).

The term "at risk" in connection with the present prophylactic treatment method means that an individual has an increased probability of contracting a particular infection as compared to the majority of healthy individuals in the same environment. Thus, for example, a patient with expected or likely exposure to a particular organism believed to be susceptible to compounds of the present invention whose defenses are compromised, such as by injury, surgery, or immune suppression, will be at risk of an infection. Alternatively, in cases where mere exposure to an organism creates a risk of infection by that organism such that a prudent medical doctor would believe medical intervention warranted to prevent the development of an active infection is also at risk of infection. Thus, the term "at risk" does not refer to the normal risk of infection to which all individuals are subject or even the increased risk presented by an individual's presence in a clinical setting unless the increased risk is sufficient to warrant medical intervention in the opinion of prudent medical doctors familiar with the relevant diseases and conditions.

The term "microbial infection" refers to the presence of a microbe in or on tissues of a host animal, e.g., a mammal. Preferably, but not necessarily, this will be the presence of pathogenic microbes. It can include the growth of microbes which are normally present in or on the body of a mammal, preferably including cases of excessive growth, and other situations where the elimination of the presence of the microbe is desirable (e.g., sub-clinical infections) (or prevention of establishment of the presence of the microbe). Usually, but not necessarily, a microbial infection will be a situation in which the presence of a microbial population(s) is damaging or potentially damaging to a host mammal. Thus, an animal is "suffering" from a microbial infection when excessive numbers of a microbial population are present in or on the animal's body, or when the effects of the presence of a microbial population(s) is damaging the cells or other tissue of a mammal. As an example, this description specifically applies to a bacterial or fungal infection.

The term "administration" or "administering" refers to a method of giving a dosage of an antimicrobial pharmaceutical composition to a mammal, where the method is, e.g., topical, oral, intravenous, intraperitoneal, or intramuscular. The preferred method of administration can vary depending on various factors, e.g., the components of the pharmaceutical composition, the site of the potential or actual microbial infection, the microbe involved, and the severity of an actual microbial infection.

The term "mammal" is used in its usual biological sense. Thus, it specifically includes humans, dogs, and cats, but also includes many other species. The term "warm-blooded animal" has its usual biological meaning.

As used herein, the term "antimicrobial" in connection with an agent, compound, or activity of a compound refers to an inhibition of the growth of a microbe. This explanation of this term applies also to other microbes and antimicrobial agents, e.g., "antibacterial" and "antifungal". Such agents may have either cidal or static activity. In general, if an agent is static, it means that the agent essentially stops cell growth (but does not kill the cell); if the agent is cidal, it means that the agent kills the cells (and may stop growth before killing the cells). However the term specifically distinguishes compounds which are toxic to cells in general (i.e., non-specific toxicity). Those skilled in the art are familiar with the distinction between general toxicity and a specific activity such as an antimicrobial activity.

In the context of the present invention, the term "inhibiting growth" refers to reducing the rate of growth of the relevant organism or cells as a result of the presence of a compound or compounds of the present invention under conditions which allow growth in the absence of that compound or compounds. Growth refers to an increase in the number of a particular population of an organism, thus reduction in the rate of growth means a reduction in the rate of increase of the numbers of the organism in the relevant population, which preferably is a cessation of growth. For organisms which have a mycelial or coenocytic form, growth includes increase in the physical size of the organism and/or increase in the number of nuclei. In this case, a reduction in the rate of growth refers to a reduction in the rate of increase in size and/or number of nuclei. A reduction in growth can include a reduction in the absolute numbers of an organism present and/or complete elimination of the organism from a location. Such reduction or inhibition can be monitored, for example, by the difference in turbidity of liquid cultures in the presence or absence of the inhibiting agent, or by the difference in plaque size for cultures on solid media in the presence or absence of the inhibiting agent, or by other methods well-known to those skilled in the art.

In connection with the preparation of derivatives in the present invention, the term "synthesizing" refers to the alteration of the structure of a naturally occurring molecule or of another derivative of a naturally occurring molecule by chemical synthetic methods involving creation of a CUPA compound and/or build-up from a CUPA compound. Chemical synthetic methods, as generally understood in the art, are methods involving intervention by humans resulting in alteration in the structure of the starting molecule where the alteration is not due to the direct action of a microorganism. Typically such methods involve manipulation of the parameters or conditions resulting in changes in the relative amounts of reactants and products. Such parameters and conditions can, for example, include concentrations of reactants, temperature, presence of catalyst, and removal of product. Generally, for build-up from a CUPA compound, the moieties to be added are selected to provide enhanced activity and/or improved pharmacodynamic or pharmacokinetic characteristics.

By "comprising" is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Additional features, advantages, and embodiments will be apparent from the following Detailed Description and from the claims.

DETAILED DESCRIPTION OF THE PREFERRED EMBODIMENTS

Figure 1:
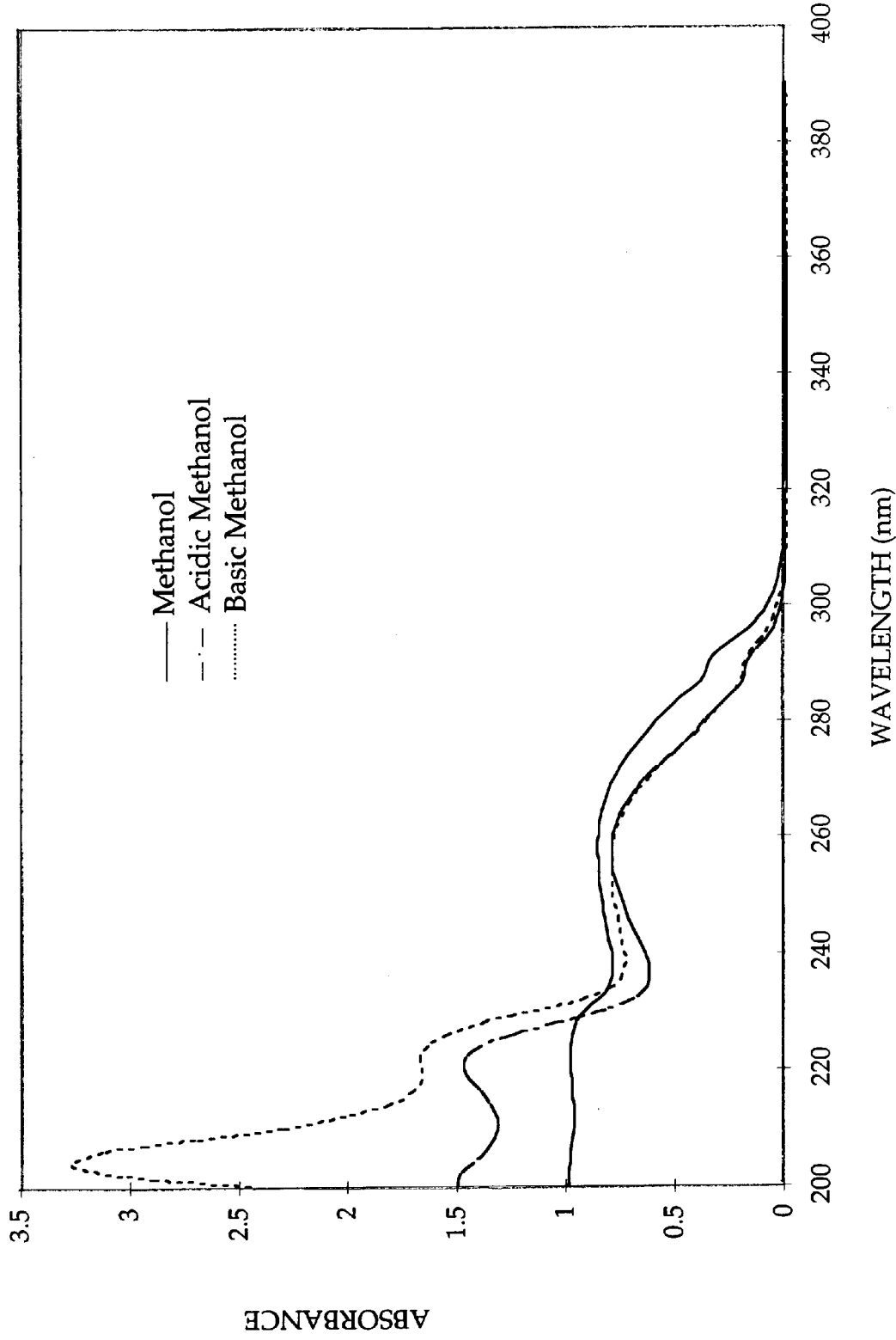
FIG. 1 is the ultraviolet absorption spectra of pacidamycin-D (25 µg/ml solution in methanol).

Compounds of the present invention isolated from natural sources were isolated from the fermentation broth of a strain of *Streptomyces coeruleorubidus* which was previously known to produce certain other pacidamycin compounds. However, the inventors found that these new active compounds can be isolated from such fermentations.

Thus, this invention concerns novel compounds, designated pacidamycin-D, pacidamycin-4N, pacidamycin-5N, and pacidamycin-5T, their production by fermentation, methods for their recovery and concentration from crude solutions, and processes for their purification. The present invention includes within its scope the antibacterial agents in dilute form, as crude concentrates, as a complex of various components, as mixtures of compounds enriched in one or more of pacidamycin-D, pacidamycin-4N, pacidamycin-5N, and pacidamycin-5T, and in purified or isolated form, including in pure form as individual components. The present invention also includes within its scope the production of the new pacidamycins by fermentation, the processes for their recovery and purification, and their use in pharmaceutical compositions and their use in the treatment of bacterial infections. In addition, the present invention concerns derivatives of the newly identified pacidamycins and of other uridyl peptide antibiotics.

Pacidamycin-D, pacidamycin-4N, pacidamycin-5N, and pacidamycin-5T are recovered from the fermentation of *Streptomyces coeruleorubidus*, NRRL 18730, (*Journal of Antibiotics*, 42:506–526, 1989) and are separated from previously described members of the pacidamycin family and further purified by chromatographic processes as described below. The chemical structure of pacidamycin-D represent a significant departure from that of the previously described pacidamycins and mureidomycins. Pacidamycin-4N and pacidamycin-5N differ from pacidamycin-4 and pacidamycin-5, respectively, in having napsamycin type N-termini, while pacidamycin-5T differs from pacidamycin-5 by containing a tyrosine instead of phenylalanine.

Production and Isolation of the New Natural Uridyl Peptide Antibiotics

The natural products compounds of the present invention were purified from the fermentation of *Streptomyces coeruleorubidus*, NRRL 18730, but it is expected that other organisms, especially other Streptomyces species and especially other strains of *Streptomyces coeruleorubidus* will produce these compounds. Thus, the present compounds could also be purified from those sources and are included within this invention. The production of these compounds can readily be determined by performing a test fermentation and purification using another strain or species as indicated.

Examples 1 and 2 below describe exemplary media which were utilized for growth of the pacidamycin-producing strain, however, other media suitable for culturing Streptomyces species can also be used. Preferably, the use of a particular medium is evaluated with respect to the efficient production of a desired compound in order to maximize recovery of the compounds. Some such media are described in the patents cited herein.

The fermentation of *Streptomyces coeruleorubidus* (NRRL 18730) was conducted according to the description in *Journal of Antibiotics*, 42:506–526, 1989 with slight modification and as further detailed in Example 1. The pacidamycins contained in the fermentation liquor can be recovered by adsorption on a polymeric resin such as Diaion® HP-20 (Mitsubishi Chemical Industries Ltd.) and selectively eluted from the resin by mixtures of water or buffer with an organic solvent such as acetone, methanol, or acetonitrile. The antibiotics contained in the eluate are further purified by selective solvent extraction and precipitation, and separated away from the previously reported pacidamycins by ion exchange chromatography using media such as Toyopearl® Sp-650M (TosoHaas). The new pacidamycins are further purified by reversed phase chromatography using media such as Amberchrom® CG-161.

In addition, while the purification process used by the inventors is described in the examples below, other purification procedures or variations known to those skilled in the art can also be utilized. In general, procedures appropriate for the purification of other pacidamycins can be used for the present compounds, understanding that the present compounds are separated from other pacidamycins at some stage of the purification. Examples of such purification methods are provided in patents cited herein and in other references known to those skilled in the art. Further, those skilled in the art will understand how to resolve the various pacidamycins, mureidomycins, and napsamycins from each other.

Thus, generally, the purification of these compounds can be performed by generally known methods, using a variety of separation media and techniques. As indicated above, these pacidamycins are generally contained in the medium, and can be initially separated from cells and cell membranes by methods such as centrifugation, filtration through high capacity media such as diatomaceous earth and/or centrifugation. They can then be recovered from the supernatant or filtrate by conventional separation methods. For example, the medium with solids removed can be processed over a chromatography medium such as ion exchange resins, including anion exchange resins, e.g., Dowex® SBR-P (Dow Chemical Co.) and cation exchange resins, e.g., Dowex® 50 W (Dow Chemical Co.) and IRC-50 (Rohm & Hass C.); non-ionic absorption resins, e.g., Amberlite® XAD-2, XAD-4, XAD-7 (Rohm and Hass Co.) Diaion® HP10, HP 20, CHP 20P, HP 50 (Mitsubishi Chemical Industries, Ltd.), active carbon absorption, silica gel, or alumina. Separations can also utilize partition or gel permeation column chromatography, e.g., using Avicel® (Asihi Chemical Industry Co. Ltd.), Sephadex® LH-20 (Pharmacia Co.), Sephadex® G-10, G-25, G-50, G-100 (Pharmacia Co.) or Toyopearl® HW-40 (Toyo Soda Manufacturing Co. Ltd.). Purifications or separations can also utilize crystallization and recrystallization. Further, purifications or separations can involve solvent extraction, preferably utilizing an organic solvent, preferably a hydrophilic organic solvent such as acetone, or a lower alcohol, preferably n-butanol.

As shown in the examples below, purification of the compounds of the present invention preferably involves a combination of centrifugation, batch and column ion-exchange chromatography, organic solvent extraction, and gel permeation chromatography.

In cases where the antibiotic compound is isolated as a salt, it may be converted to the unsalified form by conventional techniques, for example, by the use of ion-exchange resins or of adsorbents for reverse phase chromatography. conversely, the free unsalified compound may be salified by conventional means, for instance by treatment with an appropriate acid or base as described in more detail below. Likewise, suitable esters may be prepared by conventional esterification techniques, such as by reaction with an appropriate alcohol under acid catalysis.

Physico-Chemical Properties

Figure 2:
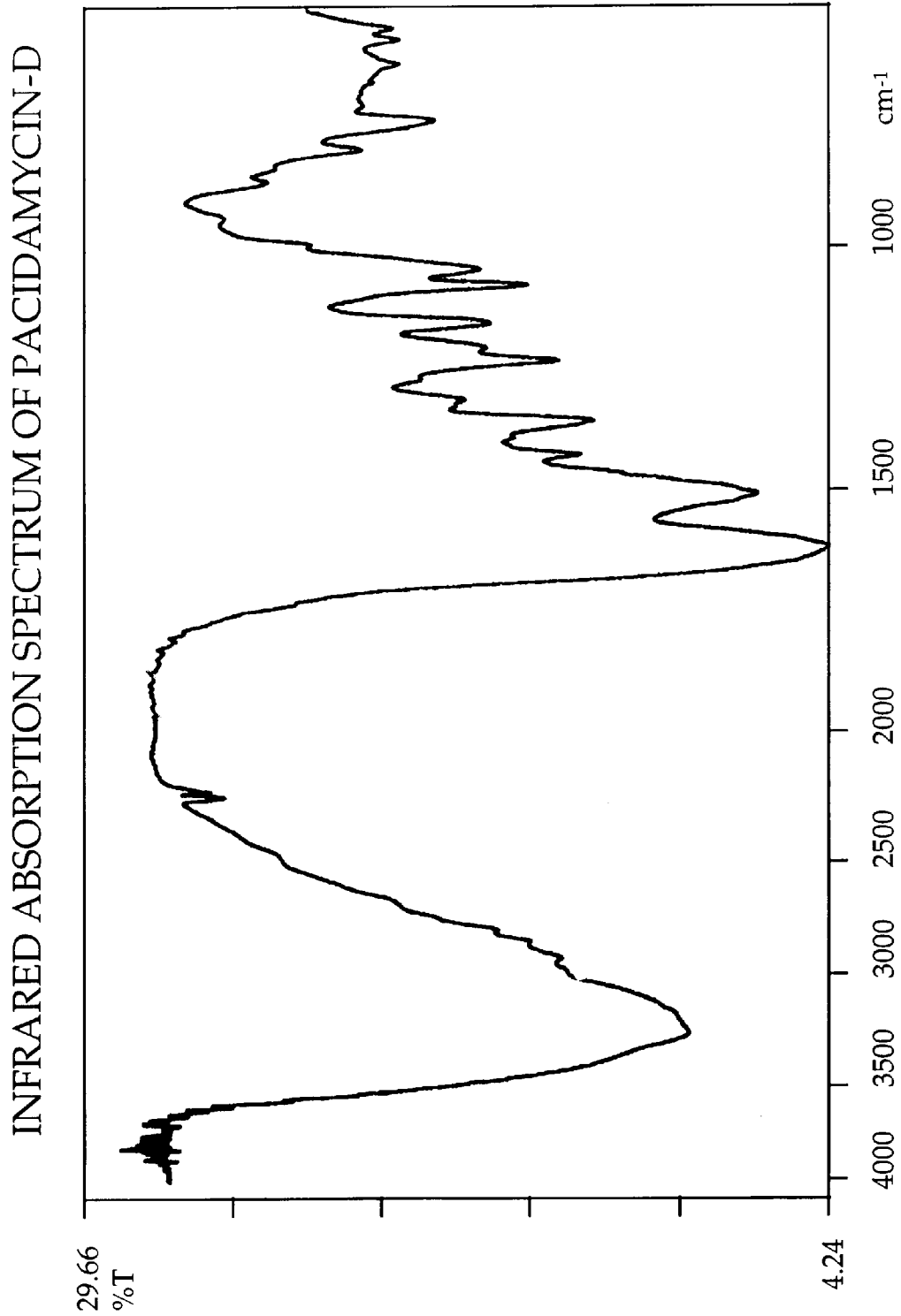
FIG. 2 is the infrared absorption spectrum of pacidamycin-D (KBr disc).
Figure 3:
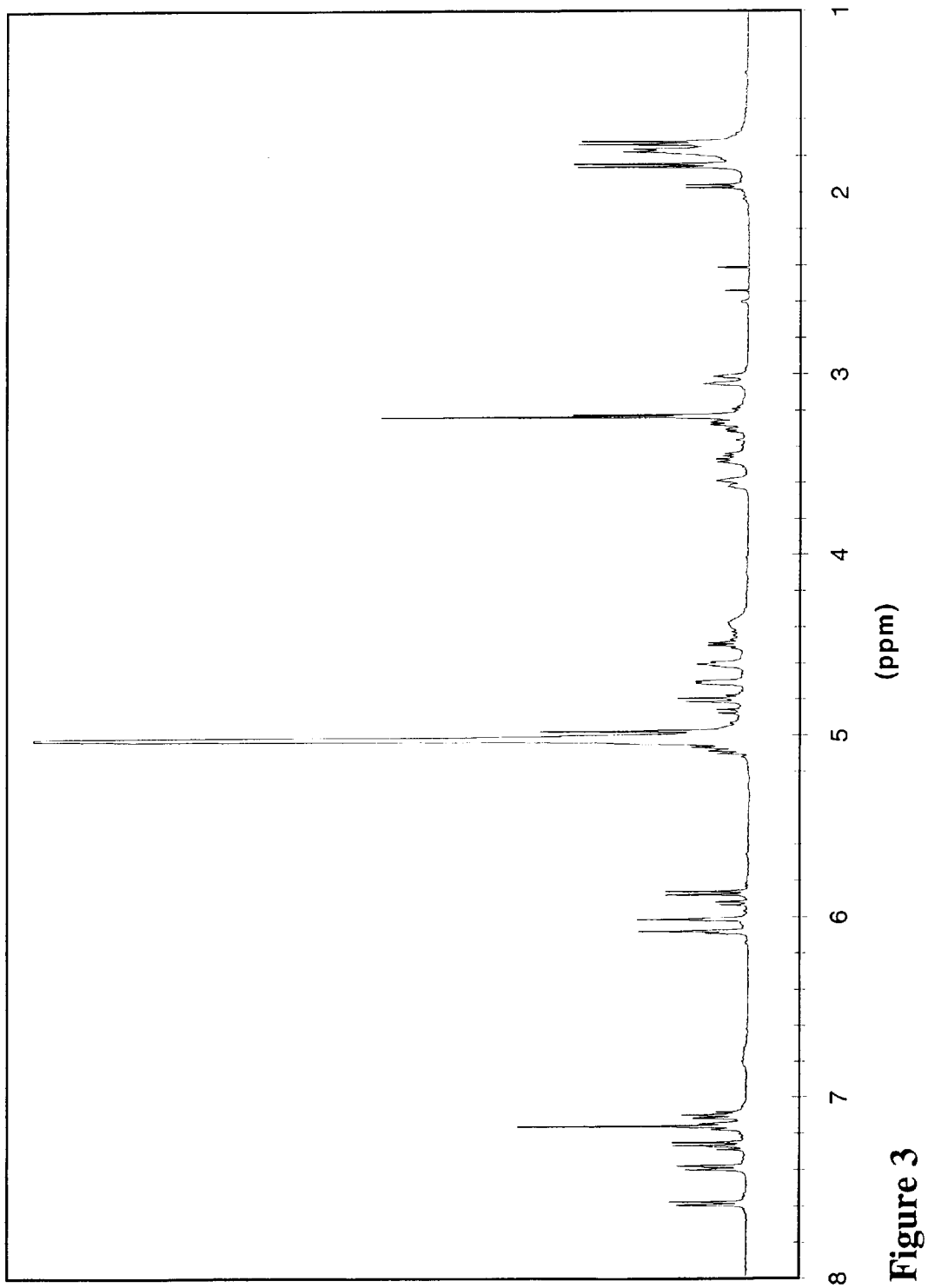
FIG. 3 is the proton magnetic resonance spectrum of pacidamycin-D (400 MHz, $D_2O$).
Figure 4:
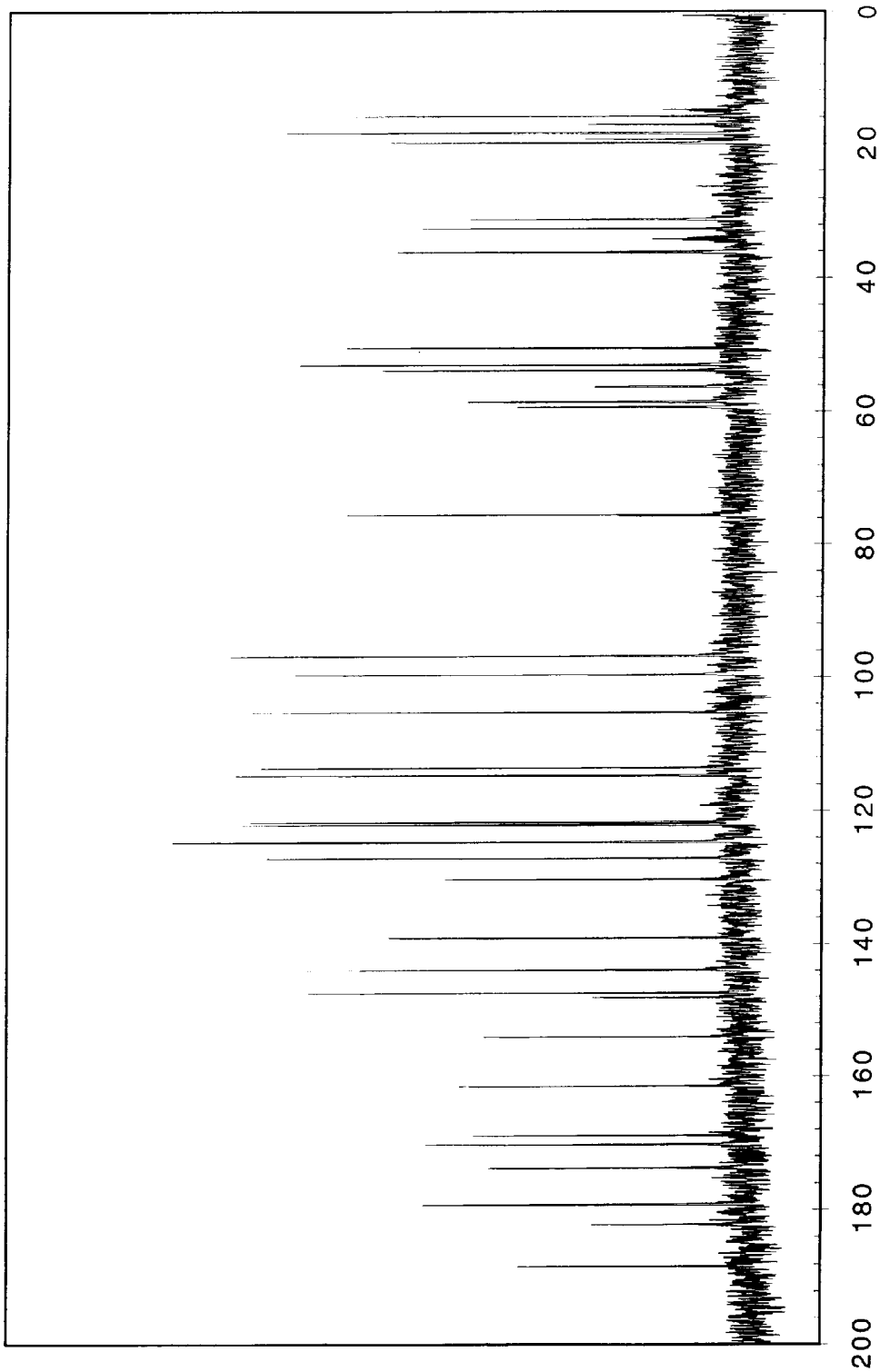
FIG. 4 is the carbon-13 magnetic resonance spectrum of pacidamycin-D (100.6 MHz, $D_2O$).

The physico-chemical properties of the new natural uridyl peptide antibiotics, pacidamycin D, pacidamycin-4N, pacidamycin-5N, and pacidamycin-5T, are described below:

Pacidamycin-D:
(1) Molecular weight: 711 ([M+H]$^+$ at m/e 712.4 was observed by Electrospray MS);
(2) Molecular formula: $C_{32}H_{41}N_9O_{10}$, exact mass for M+H was determined by high resolution FAB-MS to be 712.30803 for $C_{32}H_{42}N_9O_{10}$;
(3) Ultraviolet absorption spectrum: as shown in FIG. 1 (25 μg/ml solution in methanol, acidic methanol, and basic methanol)
(4) Infrared absorption spectrum: as shown in FIG. 2 (KBr disc);
(5) Proton magnetic resonance spectrum: as shown in FIG. 3 [400 MHz, $D_2O$, with 0.75% 3-(trimethylsilyl) 3,3,2,2-tetra-deuteropropionic acid sodium salt ($d_4$-TSPA), 23° C.];
(6) Carbon-13 magnetic resonance spectrum: as shown in FIG. 4 (100.6 MHz, $D_2O$, with 0.75% $d_4$-TSPA, 23° C.) with significant peaks and their assignments as listed below:

| 15.6 ($CH_3$) | 53.6 (CH) | 114.5 (CH) | 147.3 (C) |
|---|---|---|---|
| 18.2 ($CH_3$) | 58.3 (CH) | 121.6 (CH) | 153.9 (C) |
| 19.6 ($CH_3$) | 59.1 (CH) | 122.0 (CH) | 161.4 (C) |
| 31.1 ($CH_3$) | 75.3 (CH) | 124.5 (CH) | 168.8 (C) |
| 32.4 ($CH_3$) | 96.7 (CH) | 127.0 (CH) | 170.2 (C) |
| 36.0 ($CH_2$) | 99.4 (CH) | 130.1 (C) | 173.7 (C) |
| 50.2 (CH) | 105.0 (CH) | 138.9 (C) | 179.2 (C) |
| 52.8 (CH) | 113.4 (C) | 143.8 (CH) | 182.2 (C) |

Figure 5:
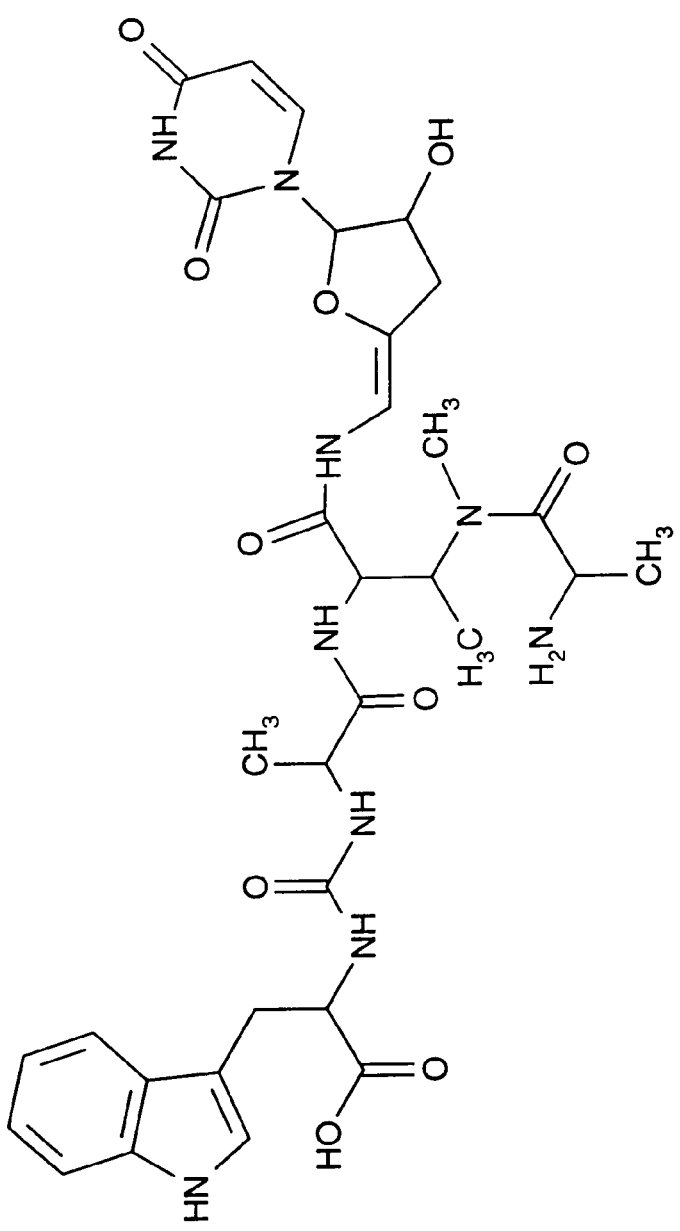
FIG. 5 is the chemical structure assigned to pacidamycin-D.

(7) Chemical structure determined as shown in FIG. 5.

Figure 6:
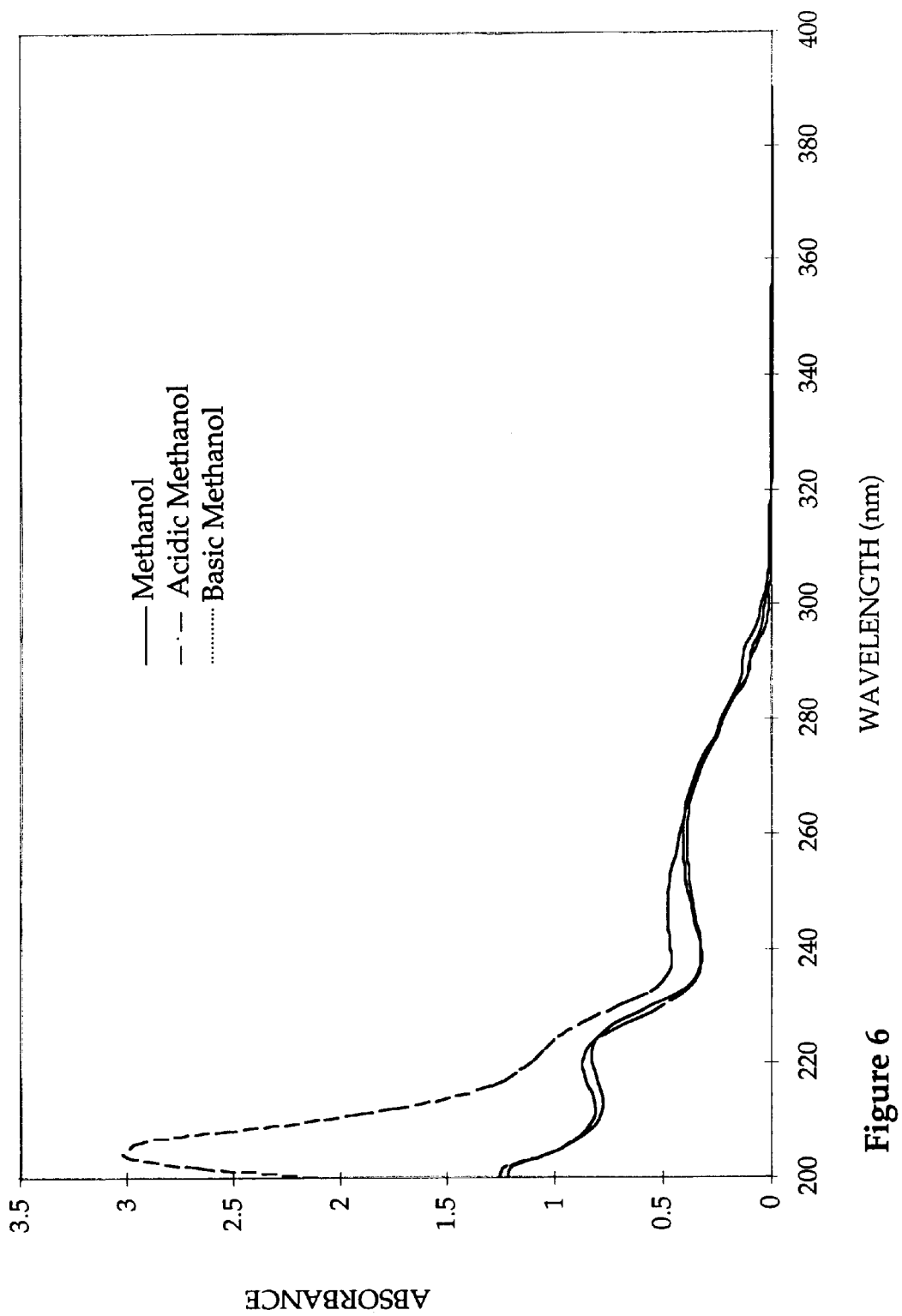
FIG. 6 is the ultraviolet absorption spectra of pacidamycin-4N (25 µg/ml solution in methanol).
Figure 7:
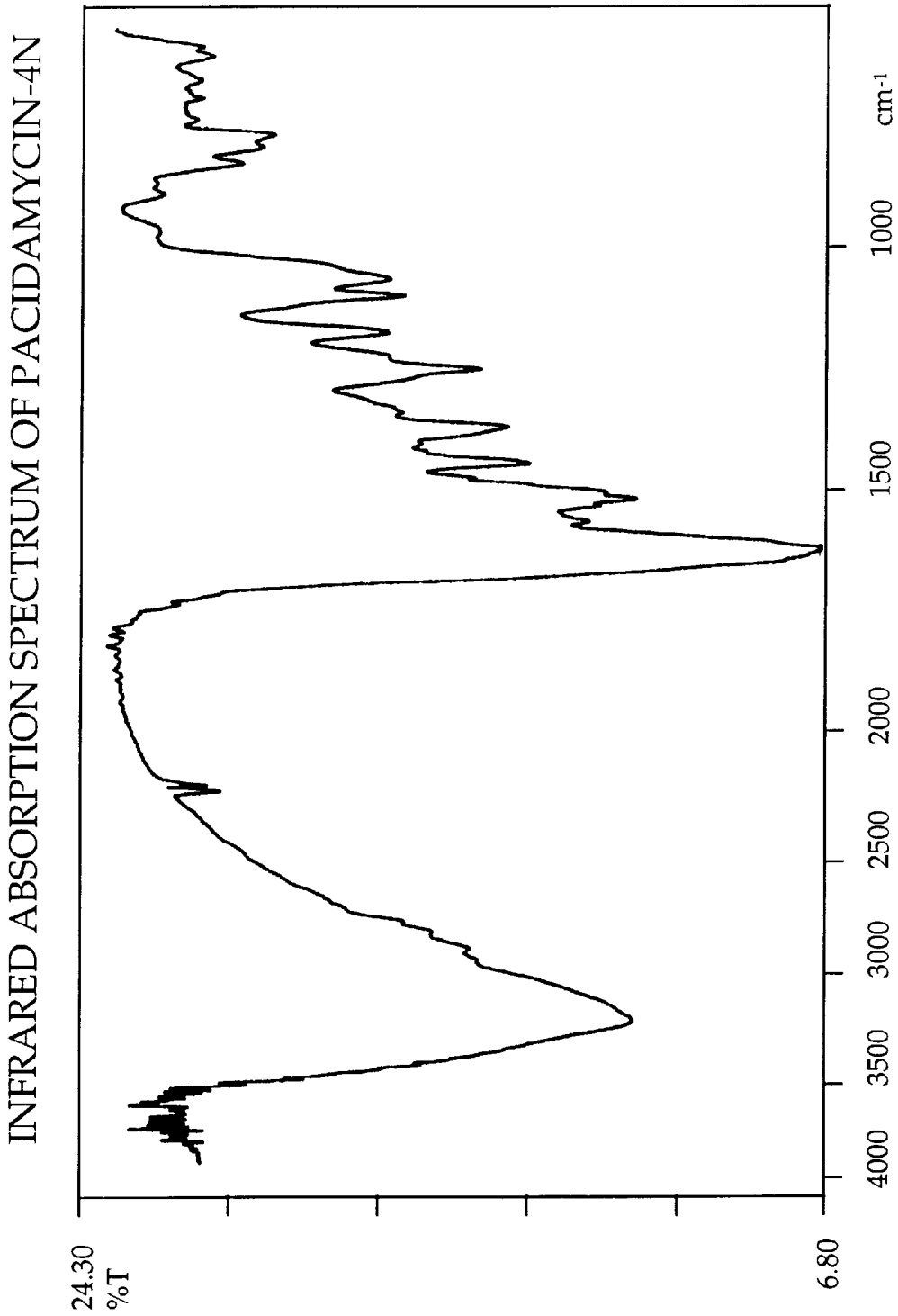
FIG. 7 is the infrared absorption spectrum of pacidamycin-4N (KBr disc).
Figure 8:
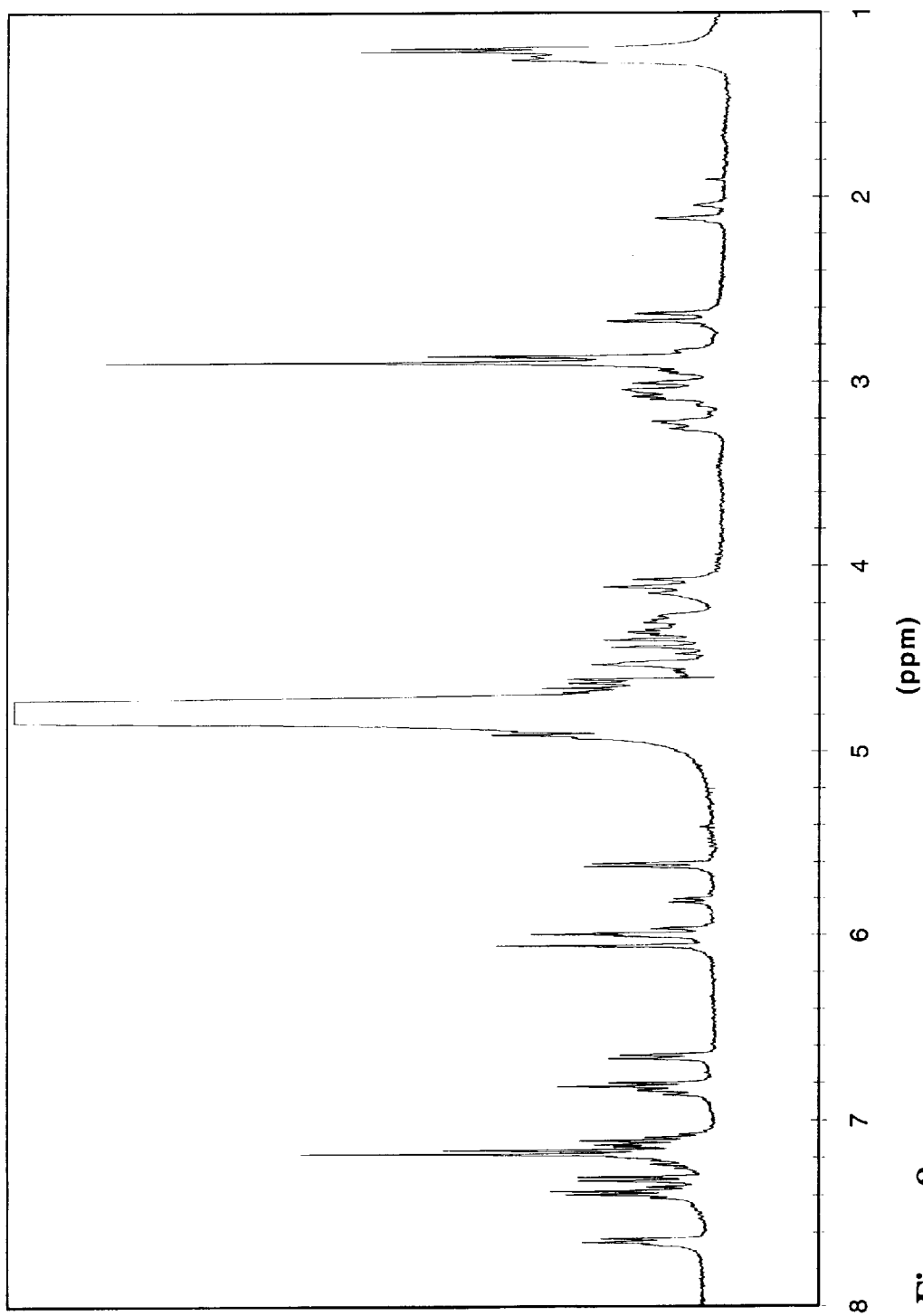
FIG. 8 is the proton magnetic resonance spectrum of pacidamycin-4N (400 MHz, $D_2O$).
Figure 9:
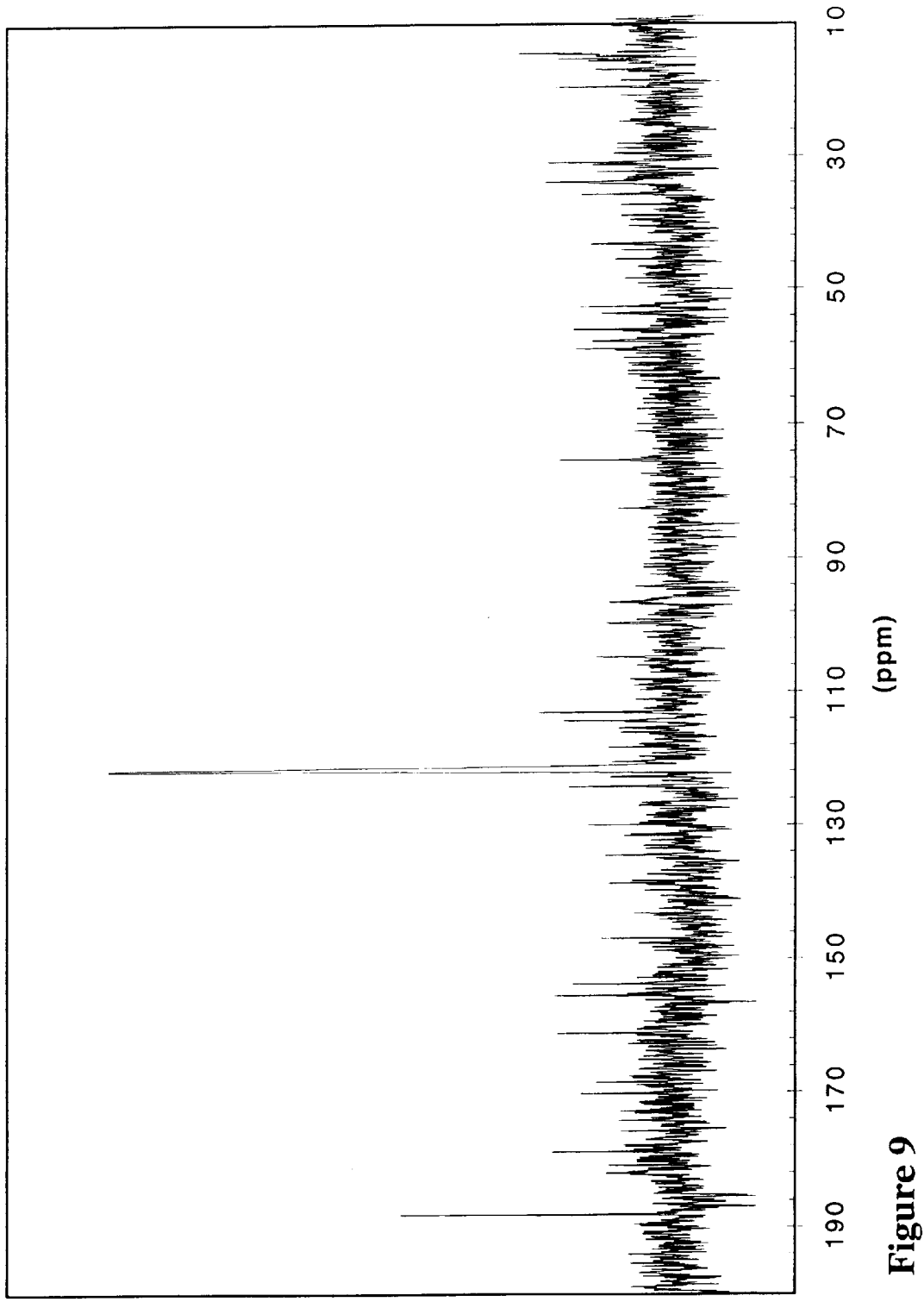
FIG. 9 is the carbon-13 magnetic resonance spectrum of pacidamycin-4N (100.6 MHz, $D_2O$).

Pacidamycin-4N:
(1) Molecular weight: 815 ([M+H]$^+$ at m/e 816.4 was observed by Electrospray MS);
(2) Molecular formula: $C_{39}H_{45}N_9O_{11}$, based on chemical structure;
(3) Ultraviolet absorption spectra: as shown in FIG. 6 (25 μg/ml solution in methanol, acidic methanol, and basic methanol);
(4) Infrared absorption spectrum: as shown in FIG. 7 (KBr disc);
(5) Proton magnetic resonance spectrum: as shown in FIG. 8 [400 MHz, $D_2O$, with 0.75% 3-(trimethylsilyl) 3,3,2,2-tetra-deuteropropionic acid sodium salt ($d_4$-TSPA), 23° C.];
(6) Carbon-13 magnetic resonance spectrum: as shown in FIG. 9 (100.6 MHz, $D_2O$, with 0.75% $d_4$-TSPA, 23° C.) with significant peaks and their assignments as listed below:

| 15.6 ($CH_3$) | 58 (CH) | 122.8 (CH) | 146.3 (C) |
|---|---|---|---|
| 19.6 ($CH_3$) | 58.2 (CH) | 124 (CH) | 153.5 (C) |
| 31.2 ($CH_2$) | 75.3 (CH) | 126.5 (CH) | 155.8 (C) |
| 31.7 ($CH_2$) | 96.5 (CH) | 130.4 (C) | 161 (C) |
| 32.8 ($CH_3$) | 99.8 (CH) | 131 (CH) | 169.7 (C) |
| 35.9 ($CH_2$) | 104.8 (CH) | 131.2 (CH) | 173.5 (C) |
| 43.5 ($CH_2$) | 113.6 (C) | 135.4 (C) | 175.6 (C) |
| 52.5 (CH) | 114.1 (CH) | 138.8 (C) | 178.1 (C) |
| 53.8 (CH) | 115.9 (CH) | 143.2 (CH) | 181 (C) |
| 55.9 (CH) | 121.5 (CH) | 143.4 (CH) | |

Figure 10:
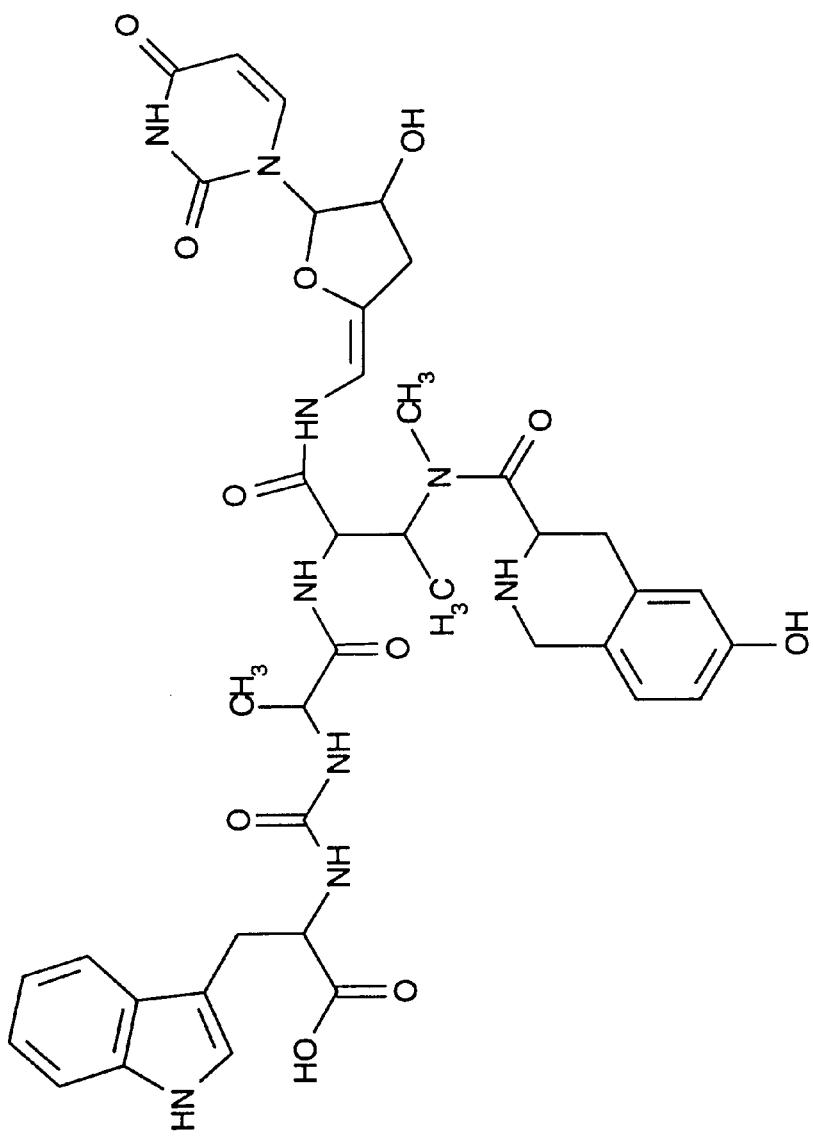
FIG. 10 is the chemical structure assigned to pacidamycin-4N.

(7) chemical structure as shown in FIG. 10.

Figure 11:
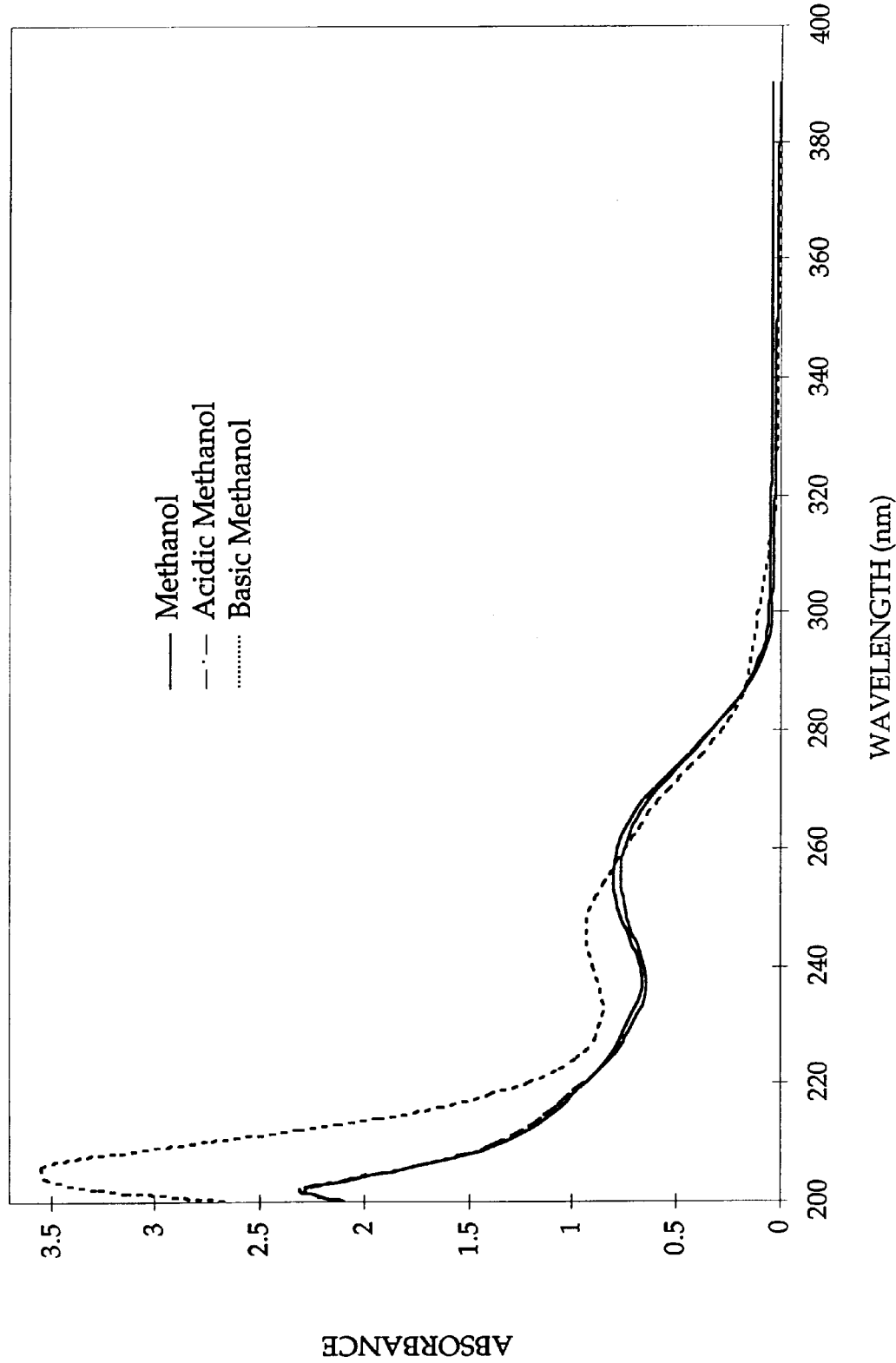
FIG. 11 is the ultraviolet absorption spectra of pacidamycin-5N (25 µg/ml solution in methanol).
Figure 12:
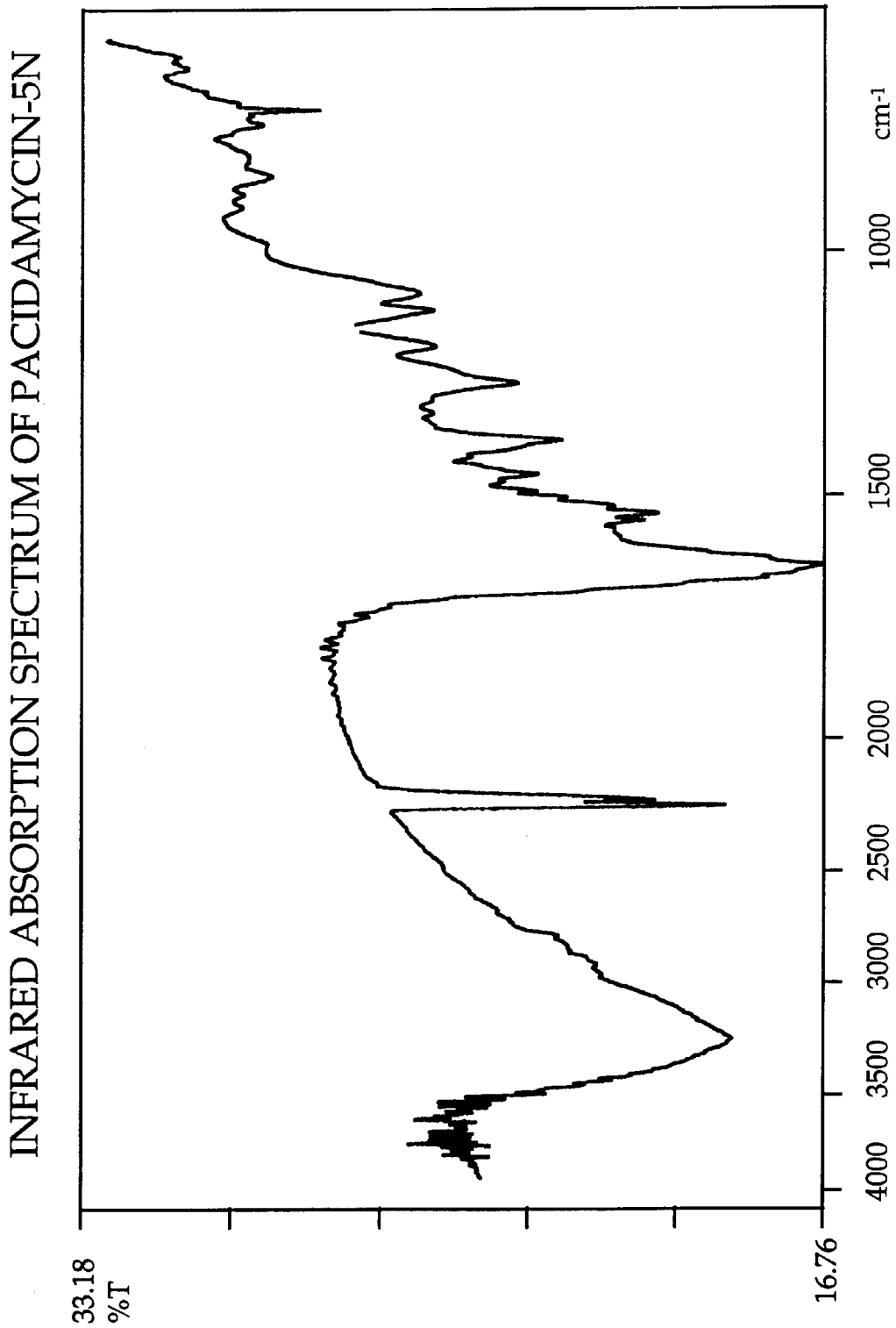
FIG. 12 is the infrared absorption spectrum of pacidamycin-5N (KBr disc).
Figure 13:
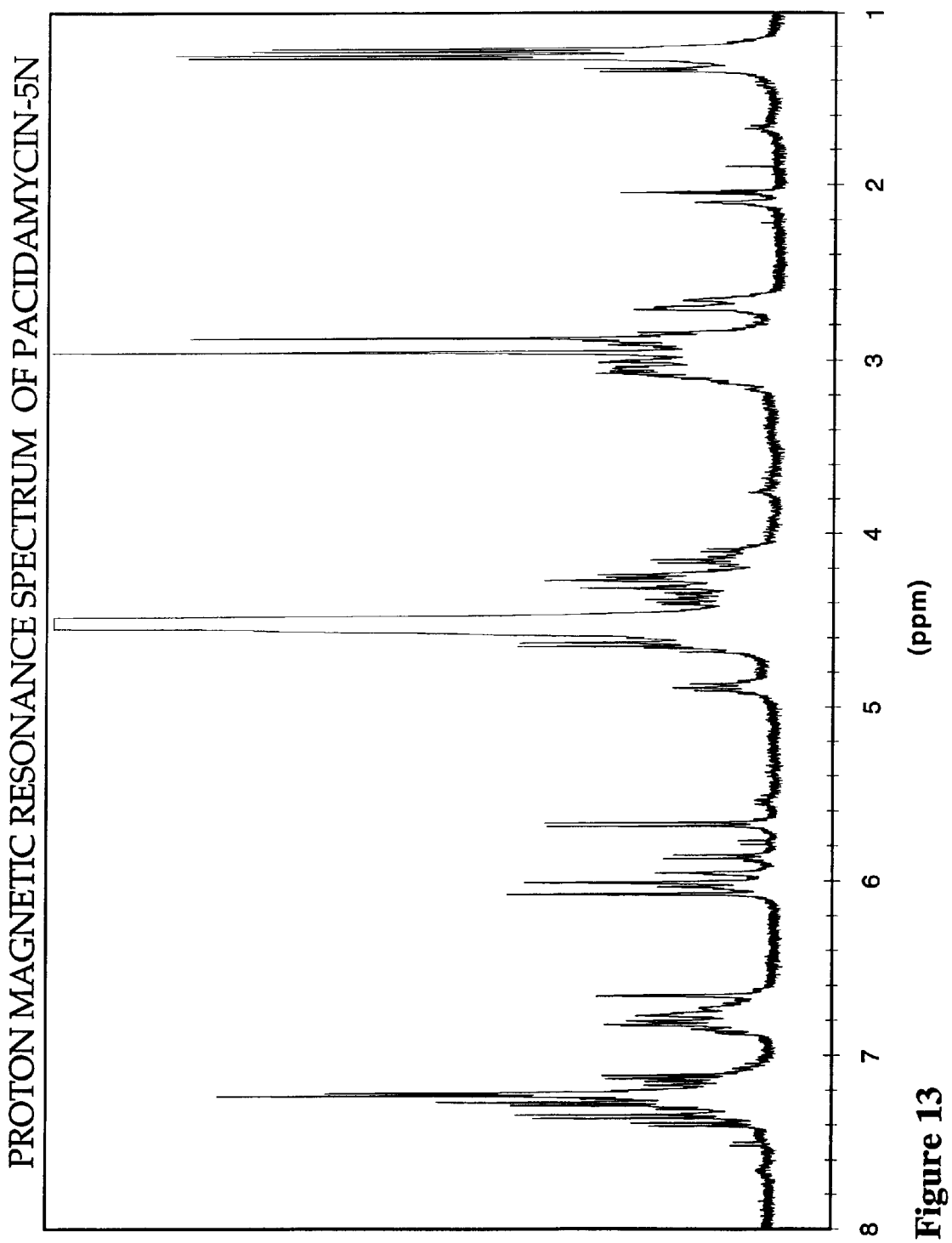
FIG. 13 is the proton magnetic resonance spectrum of pacidamycin-5N (400 MHz, $D_2O$).
Figure 14:
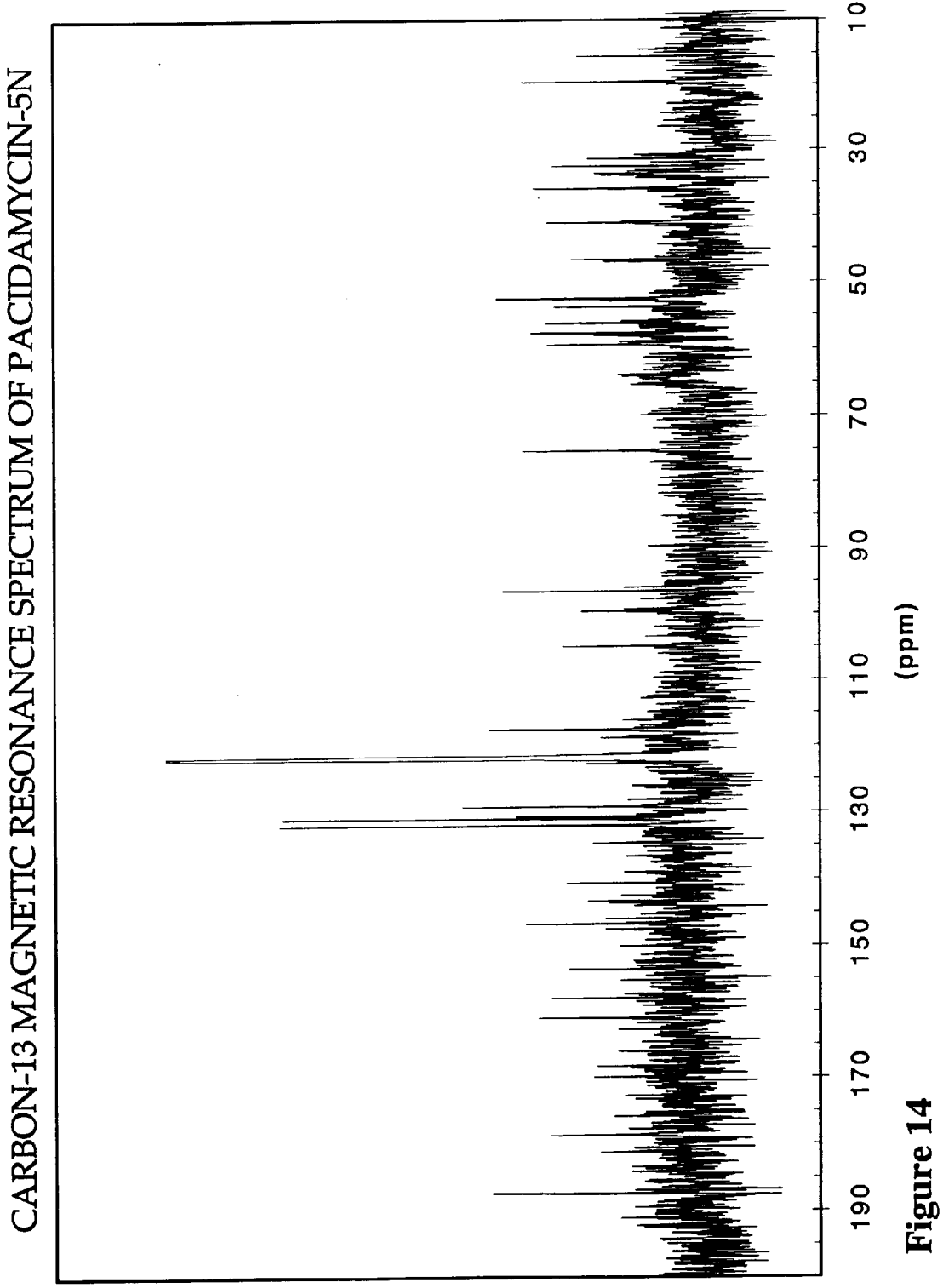
FIG. 14 is the carbon-13 magnetic resonance spectrum of pacidamycin-5N (100.6 MHz, $D_2O$).

Pacidamycin-5N:
(1) Molecular weight: 776 ([M+H]$^+$ at m/e 777.3 was observed by Electrospray MS);
(2) Molecular formula: $C_{37}H_{44}N_8O_{10}$, based on structure
(3) Ultraviolet absorption spectra: as shown in FIG. 11 (25 μg/ml solution in methanol, acidic methanol, and basic methanol)
(4) Infrared absorption spectrum: as shown in FIG. 12 (KBr disc);
(5) Proton magnetic resonance spectrum: as shown in FIG. 13 [400 MHz, $D_2O$, with 0.75% 3-(trimethylsilyl) 3,3,2,2-tetra-deuteropropionic acid sodium salt ($d_4$-TSPA), 23° C.];

(6) Carbon-13 magnetic resonance spectrum: as shown in FIG. 14 (100.6 MHz, $D_2O$, with 0.75% $d_4$-TSPA, 23° C.) with significant peaks and their assignments as listed below:

| | | | |
|---|---|---|---|
| 15.6 ($CH_3$) | 56.3 (CH) | 130.8 (CH) | 153.7 (C) |
| 19.8 ($CH_3$) | 57.8 (CH) | 131.1 (CH) | 158.1 (C) |
| 31.5 ($CH_2$) | 59.6 (CH) | 132.1 (CH) | 161.1 (C) |
| 32.6 ($CH_3$) | 75.4 (CH) | 132.6 (CH) | 168.4 (C) |
| 33.7 ($CH_2$) | 96.7 (CH) | 134.8 (C) | 170.1 (C) |
| 35.9 ($CH_2$) | 99.7 (CH) | 138.6 (C) | 176.0 (C) |
| 41.2 ($CH_2$) | 105.0 (CH) | 140.8 (CH) | 178.8 (C) |
| 52.6 (CH) | 117.7 (CH) | 143.4 (C) | 181.4 (C) |
| 53.9 (CH) | 129.3 (CH) | 146.9 (C) | |

Figure 15:
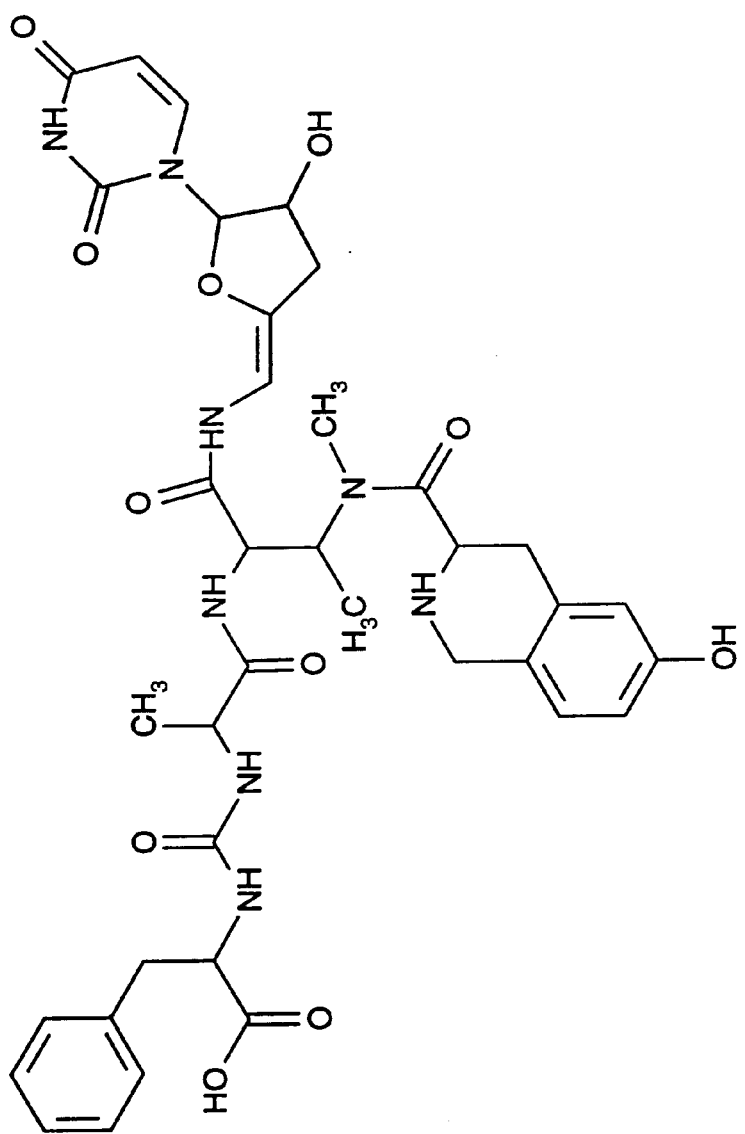
FIG. 15 is the chemical structure assigned to pacidamycin-5N.

(7) Chemical structure as shown in FIG. 15

Figure 16:
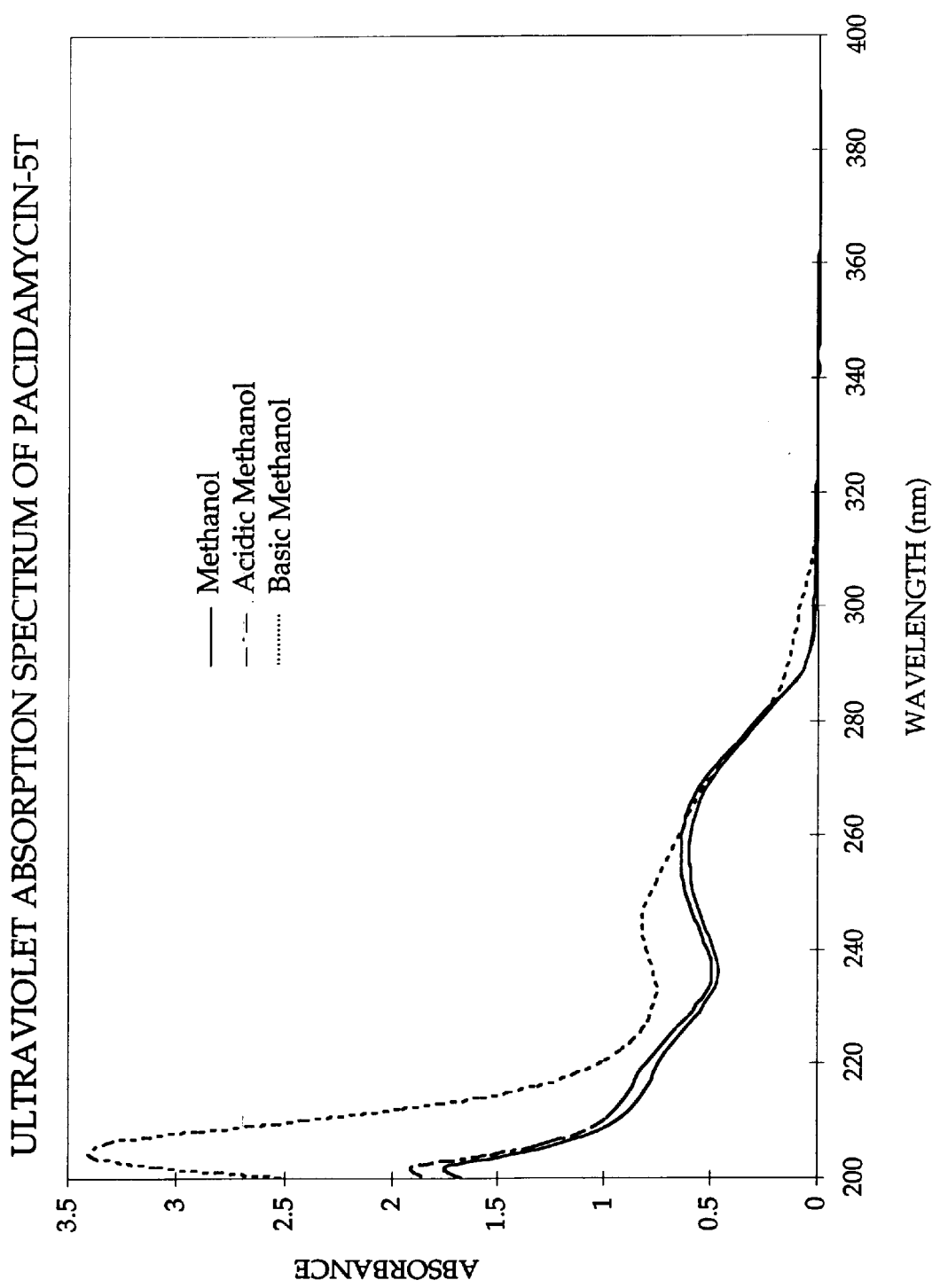
FIG. 16 is the ultraviolet absorption spectra of pacidamycin-5T (25 µg/ml solution in methanol).

Pacidamycin-5T:

(1) Molecular weight: 780 ($[M+H]^+$ at m/e 781.4 was observed by Electrospray MS);

(2) Molecular formula $C_{36}H_{44}N_8O_{12}$, based on structure (3) Ultraviolet absorption spectra: as shown in FIG. 16 (25 μg/ml solution in methanol, acidic methanol, and basic methanol)

Figure 17:
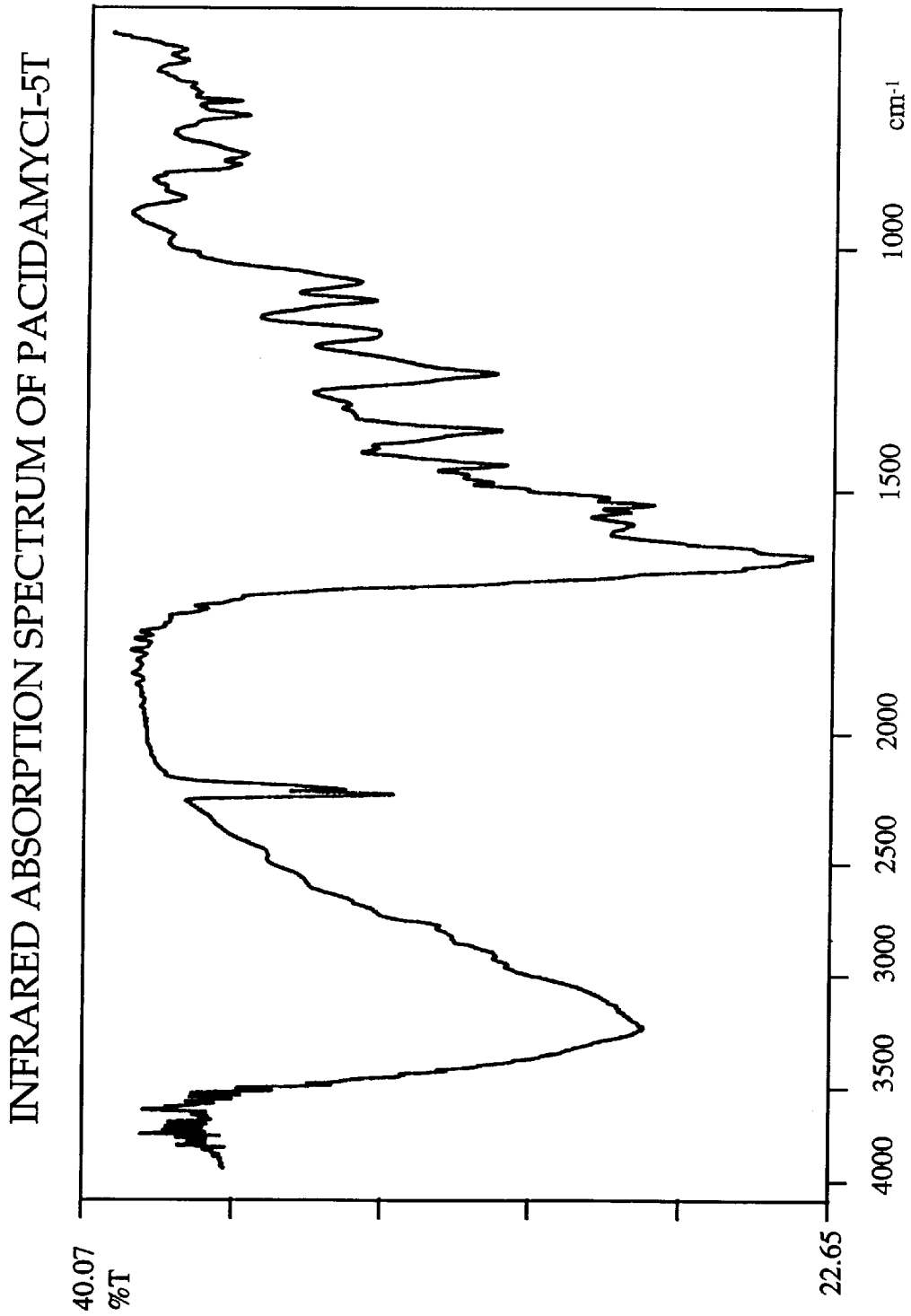
FIG. 17 is the infrared absorption spectrum of pacidamycin-5T (KBr disc).
Figure 18:
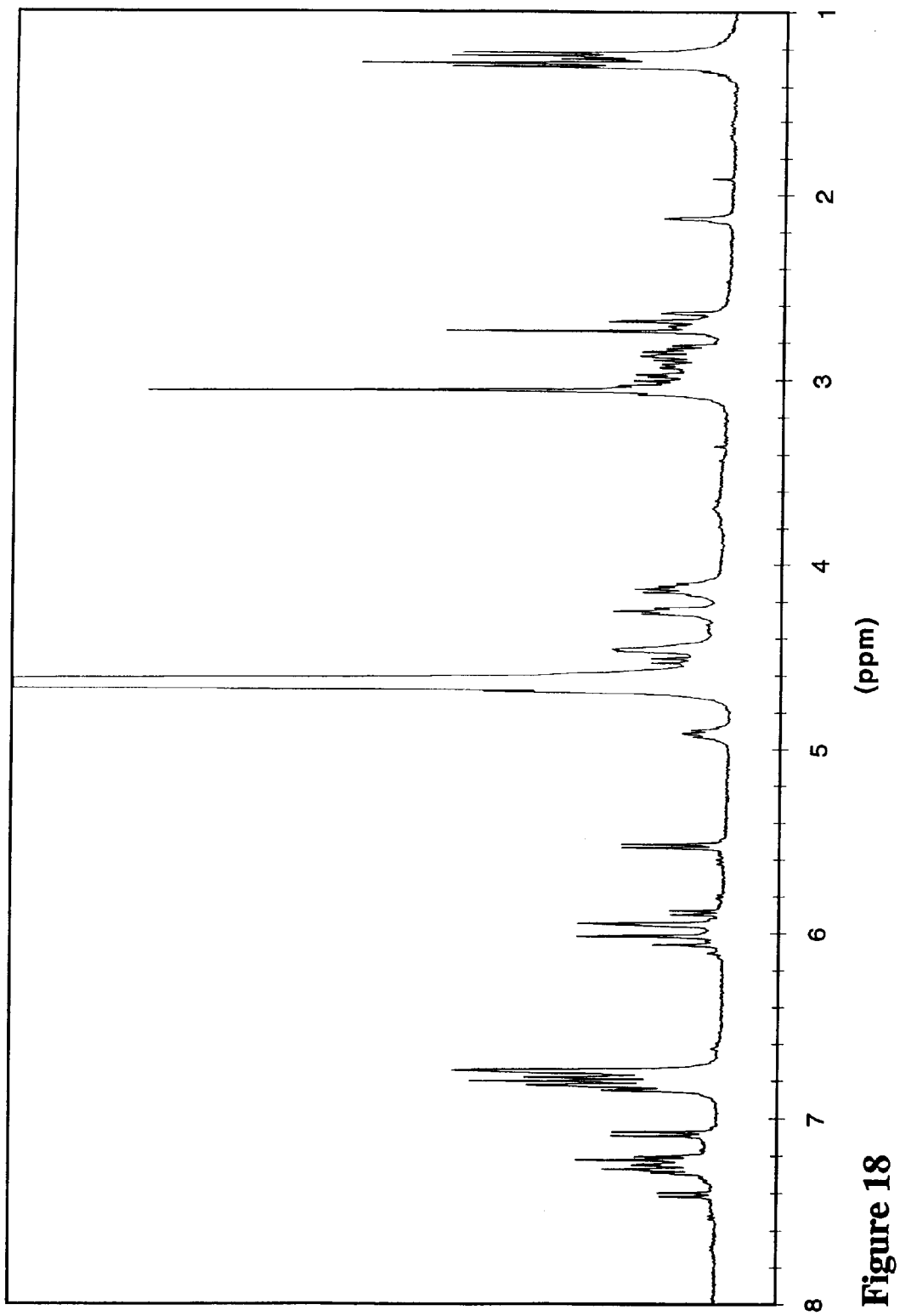
FIG. 18 is the proton magnetic resonance spectrum of pacidamycin-5T (400 MHz, $D_2O$).
Figure 19:
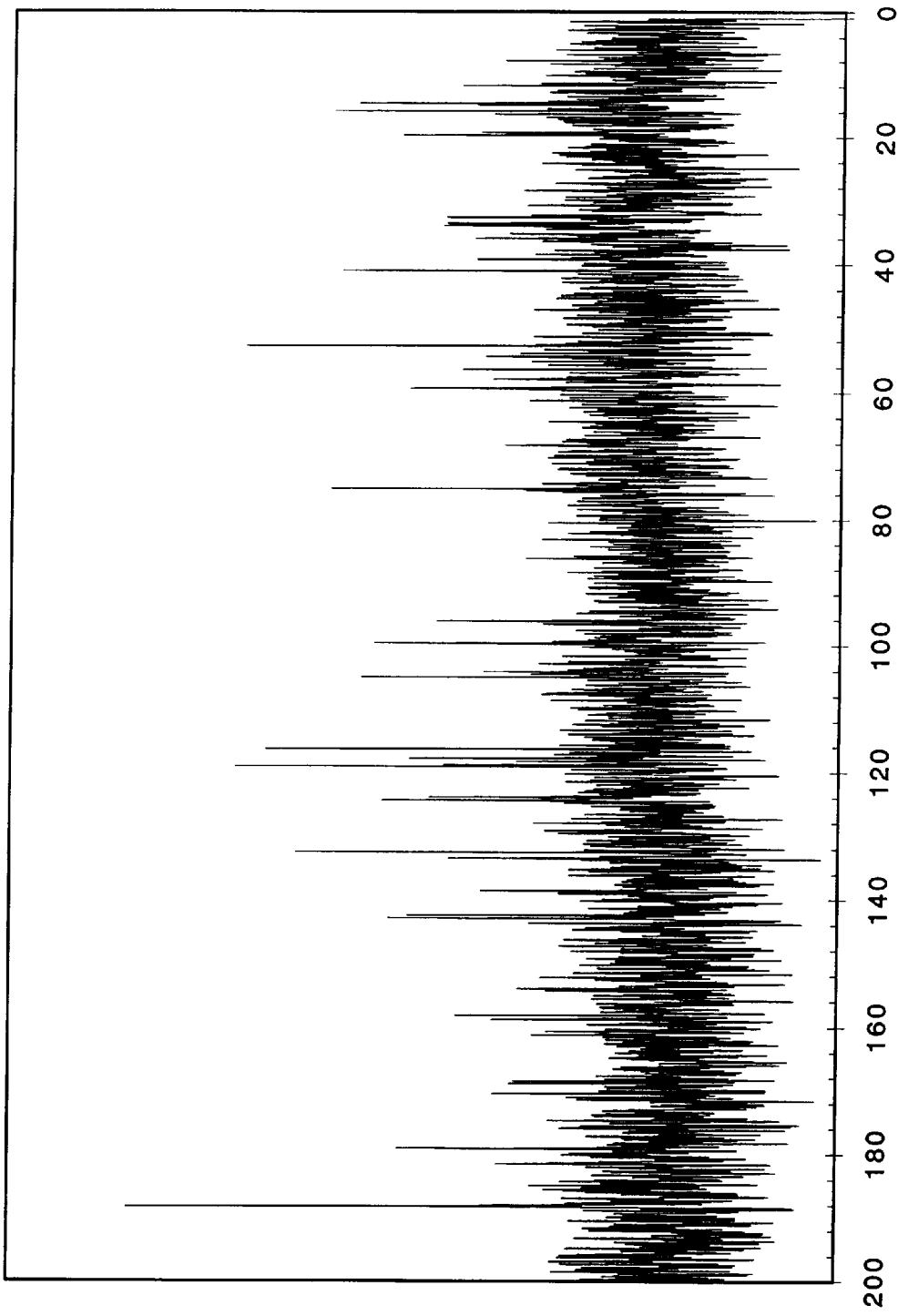
FIG. 19 is the carbon-13 magnetic resonance spectrum of pacidamycin-5T (100.6 MHz, $D_2O$).

(4) Infrared absorption spectrum: as shown in FIG. 17 (KBr disc);

(5) Proton magnetic resonance spectrum: as shown in FIG. 18 [400 MHz, $D_2O$, with 0.75% 3-(trimethylsilyl) 3,3,2,2-tetra-deuteropropionic acid sodium salt ($d_4$-TSPA), 23° C.];

(6) Carbon-13 magnetic resonance spectrum: as shown in FIG. 19 (100.6 MHz, $D_2O$, with 0.75% $d_4$-TSPA, 23° C.) with significant peaks and their assignments as listed below:

| | | | |
|---|---|---|---|
| 14.7 ($CH_3$) | 57.9 (CH) | 119 (CH) | 154.1 (C) |
| 19.7 ($CH_3$) | 59.4 (CH) | 124 (CH) | 158.3 (C) |
| 32.9 ($CH_3$) | 75.3 (CH) | 124.4 (CH) | 158.9 (C) |
| 34.1 ($CH_2$) | 96.2 (CH) | 132.7 (CH) | 161 (C) |
| 39.4 ($CH_2$) | 99.7 (CH) | 133.6 (CH) | 168.6 (C) |
| 41.1 ($CH_2$) | 105.1 (CH) | 138.8 (C) | 169 (C) |
| 52.8 (CH) | 116.5 (CH) | 138.9 (C) | 170.6 (C) |
| 54.5 (CH) | 117.9 (CH) | 142.6 (C) | 179.2 (C) |
| 56.4 (CH) | 118.9 (CH) | 143.8 (CH) | 181.6 (C) |

Figure 20:
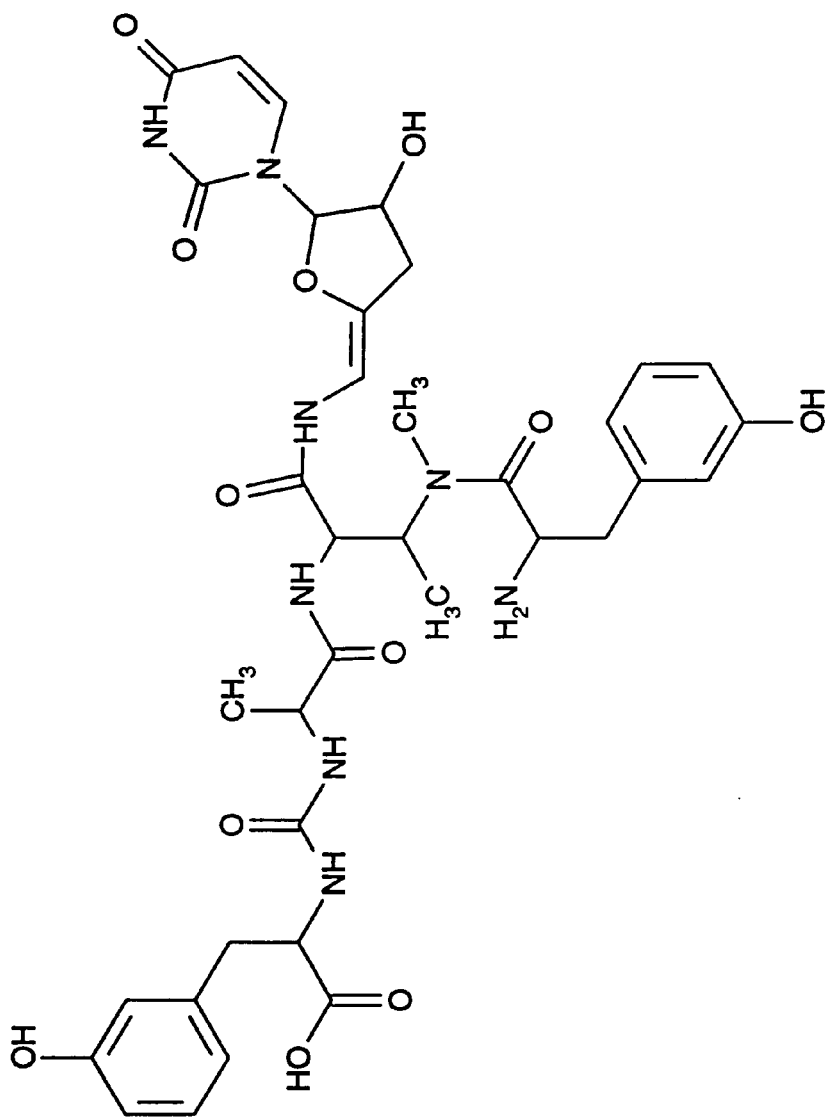
FIG. 20 is the chemical structure assigned to pacidamycin-5T.

(7) Chemical structure as shown in FIG. 20.

Enzymatic Cleavage Of Pacidamycin

Figure 21:
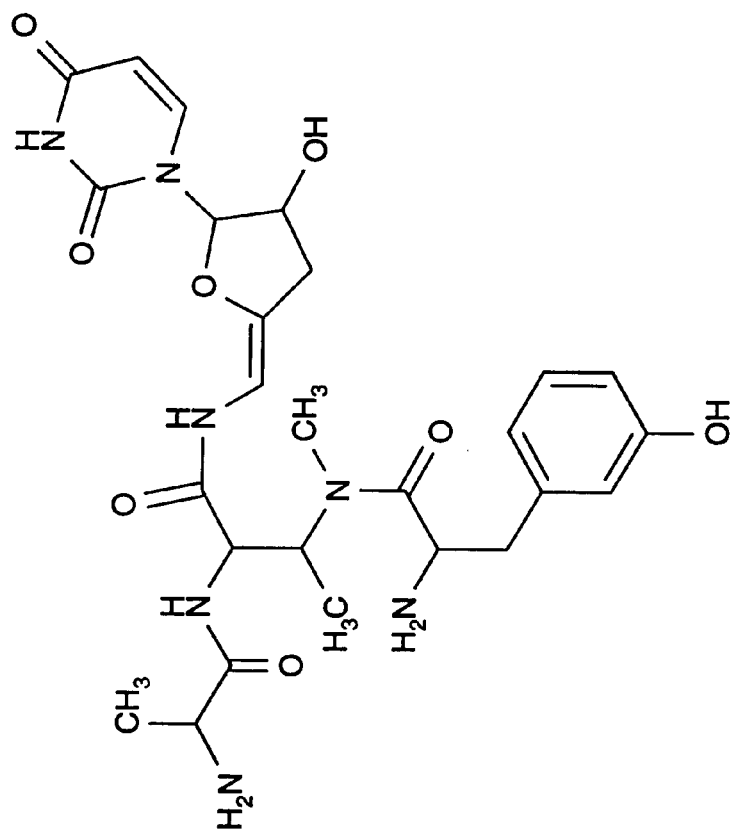
FIG. 21 is the chemical structure of the CUPA compound derived from pacidamycin 4.

Selective removal of terminal amino acids of a variety of uridyl peptide antibiotics, e.g., pacidamycins, mureidomycins, and napsamycins, including the novel pacidamycins identified herein and many chemically modified uridyl peptide antibiotics, are effected by carboxypeptidase. Thus, for example, the C-terminal amino acid, tryptophan, of pacidamycin-4 is cleaved by incubation with carboxypeptidase A. Subsequent decarbonylation of the urea carbonyl moiety gives the final product, a CUPA compound (FIG. 21). When pacidamycin complex containing the various components of the pacidamycins is incubated with carboxypeptidase A, CUPA is recovered as the major reaction product. The mention of carboxypeptidase is not a limiting example but other cross-functional enzymes may also be used. In addition, those skilled in the art will be able to remove the terminal amino acid by other methods, which may include non-enzymatic methods. The use of such other methods is also within the scope of this invention.

Biological Activity

In Vitro Antibacterial Evaluation

The compounds of the invention were evaluated against various bacterial strains by determining the minimum inhibitory concentration (MIC) of each compound with respect to each strain. The MIC is defined as the lowest concentration of drug which prevents the growth of the bacteria. A variety of different Gram-negative and Gram-positive bacterial species and strains can be selected for assay purposes depending on the particular desired application.

The susceptibility assay is performed in Mueller Hinton broth using a microdilution technique in a final test volume of 100 μl using 96-well microtiter plates. Test compounds are prepared in Mueller-Hinton broth at a concentration equivalent to 2-fold the desired final concentration.

The bacterial inoculi are prepared as follow. Bacterial strains are grown overnight at 35° C. on Tryptic Soy agar (TSA). For each strain, one isolated colony is used to inoculate a volume of 8 ml of Mueller Hinton broth and these cultures are incubated overnight (20 h) at 35° C. in a shaking incubator. Culture are then diluted 1:10 and allow to grow for an additional one hour at 35° C. in a shaking incubator. The inoculum used for the susceptibility assay is prepared by diluting the early log-phase (1 h) culture 1:2000 with fresh Mueller Hinton broth. A 50 μl volume of the inoculi, and a 50 μl solution of the test compound prepared as described above is added to each well. This procedure results in an inoculum of approximately $5 \times 10^5$ CFU/ml.

After incubation for 20 h at 35° C., the absorbance of the cultures in each is read, e.g., using the Thermo$_{Max}$ microtiter plate reader (Molecular Devices) at 650 nm. The MIC is defined as the lowest concentration of compounds which prevents growth of the microorganism and therefore results in a final absorbance equal to that of the drug-free (e.g., test compound free) control. The results are summarized in Table I.

TABLE I

In Vitro Antibacterial Activities of the Pacidamycins

Minimal Inhibitory Concentration, MIC (μg/ml)

| Organism | Pacidamycin-1 | Pacidamycin-4 | Pacidamycin-D | Pacidamycin-4N | Pacidamycin-5N | Pacidamycin-5T | CUPA |
|---|---|---|---|---|---|---|---|
| P. aeruginosa ATCC 27853 | 4 | 16 | 16 | 64 | >500 | >500 | 128 |
| P. aeruginosa UPA res. | >250 | >250 | >256 | >256 | >500 | >500 | >256 |
| P. aeruginosa 799/61 | 1 | 2 | 4 | 4 | 64 | 125 | 64 |
| X. maltophilia ATCC 13637 | >250 | — | — | — | >500 | >500 | — |
| E. coli ATCC 25922 | >250 | 64 | — | — | >500 | >500 | — |

TABLE I-continued

In Vitro Antibacterial Activities of the Pacidamycins

| | Minimal Inhibitory Concentration, MIC (µg/ml) | | | | | | |
|---|---|---|---|---|---|---|---|
| Organism | Pacida-mycin-1 | Pacida-mycin-4 | Pacidamy cin-D | Pacida-mycin-4N | Pacida-mycin-5N | Pacida-mycin-5T | CUPA |
| S. aureus ATCC 29213 | >250 | >250 | — | — | >500 | >500 | — |
| S. epidermidis ATCC 31432 | >250 | >250 | — | — | >500 | >500 | — |
| E. faecalis ATCC 29212 | 64 | 64 | — | — | >500 | >500 | — |

Pharmaceutical Applications and Preparations

According to this invention, a therapeutically or pharmaceutically effective amount of a compound of the present invention is administered to a mammal suffering from bacterial infection, in an amount effective to at least partially relieve the infection. Especially important are infections resulting from strains having similar activity to strains such as *Pseudomonas aeruginosa* ATCC 27853.

The compositions containing the compound(s) of the invention can be administered for prophylactic and/or therapeutic treatments. In therapeutic applications, the compositions are administered to a patient already suffering from an infection, as described above, in an amount sufficient to cure or at least partially alleviate one or more symptoms of the infection. An amount adequate to accomplish this is termed as a "therapeutically effective amount or dose." Amounts effective for this use will depend on the severity and course of the infection, previous therapy, the patient's health status and response to the drugs, and the judgment of the treating physician.

In prophylactic applications, compositions containing a compound or composition containing a compound of the invention are administered to an animal, preferably a person, susceptible to or otherwise at risk of a particular infection. An amount of the compound sufficient to prevent development of an infection of the animal by a susceptible bacterium is preferred. Such an amount is termed a "prophylactically effective amount or dose." In this use, the precise amounts appropriate for administration likewise depend on the patient's state of health, weight, mode and location of administration, and the like. Generally, a prophylactically effect amount will be approximately the same as a therapeutically effective amount (as defined above) for minor infections.

For therapeutic treatment, once improvement of the patient's condition has occurred, a maintenance dose is administered if necessary. Subsequently, the dosage or the frequency of administration, or both, can be reduced, as a function of the symptoms, to a level at which the improved condition is retained. When the symptoms have been alleviated to the desired level, treatment can cease. Patients can, however, require intermittent treatment on a long-term basis upon any recurrence of the disease symptoms.

While it is possible to administer the active ingredient of this invention alone, it is preferable to present it as part of a formulation or pharmaceutical composition. The formulations of the present invention comprise at least one compound or inhibitor of this invention in a therapeutically or pharmaceutically effective dose together with one or more pharmaceutically or therapeutically acceptable carriers.

Pharmaceutical compositions are prepared in a manner and with components suitable for therapeutic use, preferably for administration to a human. In general, this means that the composition will be sterile and free from components and/or contaminants which would be unacceptable for such use. Preferably, the composition and the individual components are prepared in a manner satisfying the usual regulatory requirements, e.g., requirements of the United States Food and Drug Administration. In certain embodiments, the composition is prepared in a manner and with components suitable for internal administration, preferably in a human.

Solid carriers include, e.g., starch, lactose, dicalcium phosphate, microcrystalline cellulose, sucrose, and kaolin, and optionally other therapeutic ingredients. Liquid carriers include, e.g., sterile wateer, polyethylene glycols, non-ionic surfactants, and edible oils such as corn, peanut and sesame oils. In addition, various adjuvants such as are commonly used in the art may be included. For example: flavoring agents, coloring agents, preservatives, and antioxidants, e.g., vitamin E, ascorbic acid, BHT and BHA. Various other considerations are described in Gilman et al. (eds.) (1990) Goodman and Gilman's: The Pharmacological Basis of Therapeutics, 8th Ed., Pergamon Press; and Remington's supra. Methods for administration are discussed therein, e.g., for oral, intravenous, intraperitoneal, or intramuscular administration, and others. Pharmaceutically acceptable carriers will include water, saline, buffers, and other compounds described, e.g., in the MERCK INDEX, Merck & Co., Rahway, N.J. Generally, preferred routes of administration are intravenous and intraperitoneal.

These pharmacological compositions can be in a variety of forms. These include, for example, solid, semi-solid and liquid dosage forms, such as tablets, pills, powders, liquid solutions or suspensions, liposomes, injectable and infusible solutions. The preferred form depends on the intended mode of administration and therapeutic application. Generally, a pharmacologically acceptable salt of the compound will be used to simplify preparation of the composition. Preferred salts include sodium, potassium, arginine, glycine, alanine, threonine. These are prepared, preferably, in water suitably mixed with a surfactant such as hydroxypropylcellulose.

Since the compounds of the present invention may be amphoteric in character, they form salts and esters and these salts and esters also form part of the present invention. The nature of such salts and esters is not critical, except that, where they are to be used for medicinal or veterinary purposes, they must be medicinally acceptable, i.e. they must not, or must not to a significant extent, either have such increased toxicity or have such reduced activity, as compared with the free unsalified or unesterified compound, as to make the therapeutic use inappropriate. Those skilled in the art will readily understand the levels of toxicity or reduced activity which would preclude therapeutic use of the compounds. Preferably, the salt or ester form will not have increased toxicity or reduced activity.

Examples of suitable acids for the formation of such salts include: inorganic acids, such as hydrochloric acid, sulfuric acid or phosphoric acid; organic carboxylic acids, such as acetic acid, citric acid, tartaric acid, malonic acid, maleic acid, malic acid, fumaric acid, itaconic acid, citraconic acid or succinic acid; and organic sulfonic acids, such as methanesulfonic acid, ethanesulfonic acid, hydroxyethanesulfonic acid, camphorsulfonic acid, benzenesulfonic acid, naphthalenesulfonic acid or p-toluenesulfonic acid.

Examples of suitable esters include: $C_1$–$C_6$, more preferably $C_1$–$C_4$, alkyl esters, for example the methyl, ethyl, propyl, iso-propyl, n-butyl, iso-butyl, sec-butyl, tert-butyl, pentyl and hexyl esters; aralkyl and diarylalkyl esters, such as the benzyl, p-methoxybenzyl, p-nitrobenzyl and benzyhydryl esters; acyloxy-alkyl esters, in which the alkyl substituent are $C_1$–$C_4$, such as the acetoxy-methyl, 1-(acetoxy) ethyl, pivaloyloxymethyl, 1-(pivaloyloxy)ethyl, (cyclohexyl-carbonyloxy)methyl, (1-methylcyclohexylcarbonyloxy)methyl; alkoxycarbonyloxyalkyl esters in which the alkoxy and alkyl parts are both $C_1$–$C_6$, especially 1-(alkoxycarbonyloxy)ethyl esters, such as the 1-(methoxycarbonyloxy)ethyl, 1-(ethoxycarbonyloxy)ethyl, 1-(t-butoxycarbonyloxy)ethyl esters, 1-(cyclohexyloxycarbonyloxy)ethyl; and other specific esters, such as the phthalidyl, substituted phthalidyl, phenacyl, substituted phenacyl (e.g., p-nitrophenacyl) and (5-methyl-2-oxo-1,3-dioxol-4-yl)methyl esters. The esters are preferably formed at the carboxy group.

The carboxy group may also form salts with appropriate bases. The nature of such salts is likewise not critical, provided that, where they are to be used for therapeutic purposes, the salts are pharmaceutically acceptable. Examples of salts include: metal salts, especially alkali metals and alkaline earth metals, such as lithium, sodium, potassium, calcium and magnesium salts; the ammonium salt; salts with organic amines, such as cyclohexylamine, diisopropylamine or triethylamine; and salts with basic amino acids, such as lysine or arginine.

Depending on the specific conditions being treated, such agents may be formulated and administered systematically or locally. Techniques for formulation and administration may be found in Remington's Pharmaceutical Sciences, 18th ed., Mack Publishing Co., Easton, Pa. (1990). Suitable routes may include oral, rectal, transdermal, vaginal, transmucosal, or intestinal administration; parenteral delivery, including intramuscular subcutaneous, intramedullary injections, as well an intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

In soft capsules, the active compounds may be dissolved or suspended in suitable liquids, such as fatty oils, liquid paraffin, or liquid polyethylene glycols. In addition, stabilizers may be added.

EXAMPLES

The present invention will be more fully described in conjunction with the following specific examples which are not to be construed in any way as limiting the scope of the invention.

Example 1

Production of the new pacidamycins by the fermentation of *Streptomyces coeruleorubidus* NRRL 18730.

A three stage seed preparation was used to inoculate the production fermenter. The media used for growing the seed was prepared according to the following formula and sterilized.

| Seed Medium | |
|---|---|
| Ingredients | Conc. (grams/liter) |
| Glucose Monohydrate | 10 |
| Soluble Starch | 15 |
| Yeast Extract | 5 |
| Casitone | 5 |
| $CaCO_3$ | 1 |
| $H_2O$ | |
| pH to 7.0 prior to sterilization | |

The seed build up started by inoculating a fresh culture of *Streptomyces coeruleorubidus* NRRL18730 into four 250-ml baffled Erlenmeyer shake flasks, each containing 100 ml of the sterilized seed media. The flasks were incubated on a rotary shaker (250 rpm) at 28° C. for 36 hours to give the stage-1 seed. The stage-1 seed (200 ml) was inoculated into two 4000-ml flasks each containing 1000 ml of the seed media. The flasks were incubated under the same condition as the above for 27 hours to give the stage-2 seed. The stage-2 seed (2000 ml) was inoculated into 22 liters of the seed media in a 28-liter fermenter. The fermenter was maintained at 28° C., 300 rpm agitation, 10 slpm aeration, and 4.0 psi backpressure for 26 hours to give the stage-3 seed.

The stage-3 seed was inoculated into a 300-liter reactor, containing 230 L of the production media prepared according to the following formula where part A of the media components were sterilized together in the 300-liter reactor and part B was sterilized separately and was added to part A after both have cooled down.

| Production Medium A | |
|---|---|
| Ingredients | Conc. (g/L) |
| Part A | |
| Soytone | 10 |
| Soluble Starch | 10 |
| $H_2O$ (205 liter) | |
| Part B | |
| D-Maltose | 20 |
| Trace Element | 5 ml/L |

The fermentation was allowed to proceed with 400 rpm agitation, 100 slpm aeration, 5.0 psi backpressure, 29° C., and maintained at pH 6.5 with the addition of 6N sodium hydroxide or 30% phosphoric acid. The fermentation mash was harvested after 117 hours.

Example 2

Recovery of the bioactive components from the fermentation of *Streptomyces coeruleorubidus* NRRL 18730.

The harvested fermentation mash (220 L) was processed through a Sharples continuous flow centrifuge and the clarified culture broth was adjusted to pH 5.5. The antibiotic complex contained in the culture broth was batch adsorbed on to Diaion® HP20 (Mitsubishi) resin (5 L) by stirring overnight at 5° C. The supernatant was decanted off and the resin containing the antibiotic complex was treated with 0.1% sodium azide and stored at 5° C. before further processing.

Each 2.5 liters of the above HP-20 resin containing the antibiotic complex was slurry packed into a chromatography column (Amicon Vantage-A column, 8.9 cm ID, 0–510 cm adjustable bed height). The column was sequentially eluted at 40 ml/min with 1) water until the eluate was colorless (180 min), 2) a gradient of 0 to 15% acetone over 30 min, 3) 15% acetone (120 min), 4) gradient of 15 to 90% acetone over 300 min, and 5) 90% acetone (90 min). Fractions (800 ml each) were collected at 20 min intervals throughout the elution and were bioassayed against *Pseudomonas aeruginosa* (ATCC 27853. The desired fractions were combined and concentrated in vacuo at or below 35° C. until all organic volatiles were completely removed. The aqueous solution was adjusted to pH 5.0 and extracted twice with equal volumes of n-butanol. The combined n-butanol extract was concentrated in vacuo at or below 50° C. until most of the water was removed. The resultant precipitate of the antibiotic complex was collected by centrifugation, washed with ethyl acetate and dried under vacuum to give 8.8 g of crude antibiotic complex.

Example 3
Separation of the individual pacidamycins from the crude antibiotic complex by ion-exchange chromatography.

A 2.19 g sample of the crude antibiotic complex from above, dissolved in a mixture of 16 ml of buffer A (0.05 M NaOAc, pH 3.6) and 8 ml of acetonitrile, was top loaded on a Toyopearl® SP-650M (TosoHaas) column (2.5 cm×50 cm) which was pre-equilibrated in buffer A. Upon completion of loading, the column was eluted at 10 ml/min with a gradient from 100% buffer A to 100% buffer B (0.05 M NaOAc pH 5.6) according to the following table.

| SP-650M Column Gradient Table | | |
|---|---|---|
| Time (min) | Buffer A (pH 3.6) | Buffer B (pH 5.6) |
| 0 | 100% | 0% |
| 50 | 100% | 0% |
| 175 | 25% | 75% |
| 300 | 0% | 100% |

The fractions (2.5 min, 25 ml) collected during the elution were bioassayed against a sensitive strain of *Pseudomonas aeruginosa* 799-61 and by HPLC. For each of three parallel chromatographic runs, appropriate fractions were combined into 9 pools based on the chromatographic traces and the assay results. Three of the pools contained new pacidamycins-4N, -5N, -5T, and -D. These pools generally contained varying relative proportions of the new pacidamycins, while the other 6 pools primarily contained previously described pacidamycins-1, -4, -5, and -6. Pools from the 3 parallel runs which contained the new pacidamycins were further pooled based on chromatographic and bioassay results to provide separate pools enriched in one of the new compounds. Each pool containing the new pacidamycins was neutralized (pH 6.0–6.4) with 28% ammonium hydroxide and further purified by reversed phase column chromatography using Amberchrom® (TosoHaas) where necessary or desalted directly to give the pure pacidamycins.

Example 4
Final purification of the new pacidamycins by reversed phase column chromatography A 2500 ml pooled fraction containing primarily pacidamycin-D was loaded on an Amberchrom® column (2.5×100) equilibrated in deionized water. Upon completion of loading, the column was washed successively with 2 bed volumes of water and 2 bed volumes of 0.1 M $NH_4OAc$ (pH 7.8). It was then eluted at a flow rate of 2 ml/min with 1) a gradient of 0% to 12% $CH_3CN$ in buffer over 50 min, and 2) 12% $CH_3CN$ in buffer for 400 min. The desired fractions determined as described before were combined, concentrated to remove $CH_3CN$, and then loaded onto an Amberchrom® column (2.5×50 cm) pre-equilibrated in de-ionized water. Upon completion of loading, the column was washed with 1250 ml of de-ionized water and pacidamycin-D was eluted from the column with $CH_3CN$—$H_2O$ (1/1). After removing the acetonitrile in vacuo, the aqueous solution was freeze-dried to yield 1.14 g of pacidamycin-D.

Similarly, new uridyl peptide antibiotics, pacidamycin-4N (1.5 g), pacidamycin-5N (283 mg) and pacidamycin-5T (492 mg) were isolated from the corresponding pooled fractions.

Fractions were then repooled to provide essentially pure preparations of each of the new pacidamycins.

Example 5
Preparation of CUPA from Pacidamycin Complex (Pacidamycin-4 is Predominant Starting Material)
Note: The fermentation complex will often produce small quantities of the dihydrouracil analogs (herein referred to as DHU-analogs) of the major uracil-containing components. Their presence is evidenced by the presence of molecular ions in the mass spectrum that are 2 mass units greater then the corresponding uracil-containing component.

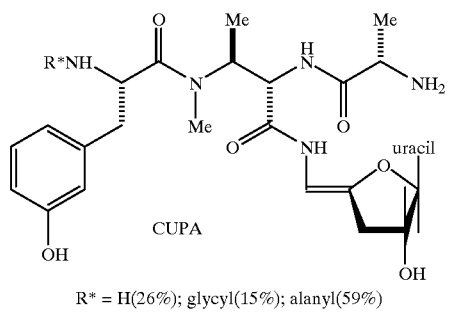

R* = H(26%); glycyl(15%); alanyl(59%)

A Hewlett-Packard HP1090 HPLC equipped with a PLRP-S reverse phase column (Polymer Laboratories, Ltd. 5 micron particle size, 150 mm×4.6 mm (I.D.)) was used for HPLC analyses of reaction mixtures. HPLC analyses were typically performed under isocratic elution conditions (15% $CH_3CN$ in 0.1 M $NH_4OAc$, pH7.8) and with diode array detection.

Pacidamycin complex (400 mg—Example 4), consisting primarily of pacidamycin-1 with some pacidamycin-4 and pacidamycin-6, was dissolved in 0.02M Tris buffer (pH 8.0) was treated with carboxypeptidase A (1700 units; Sigma Chemical Company—#C-0261). The mixture was maintained at 41° C. with agitation, and the reaction was monitored by HPLC until all starting pacidamycins were consumed (14 days). The resulting product, containing CUPA, was purified on Amberchrom (TosoHaas, 50–100 m, 40 $cm^3$ bed volume, 2.5 cm (ID)×8 cm) reverse-phase column eluting with 15% acetonitrile in 0.1 M ammonium acetate (pH 5.0). The product was further purified on a Toyopearl SP-650 (TosoHaas, 65 m, 20 $cm^3$ bed volume, 2 cm (ID)×6 cm) cation exchange column using a pH gradient (pH 4 to 9, 0.05 M phosphate buffer). The product, which eluted at pH 9.0, was further desalted on Amberchrom (40 cm³ bed volume, 2.5 cm (ID)×8 cm) and was lyophilized to give 170 mg of CUPA comprised of:

$NH_2$-CUPA: m/e 574.2 (M+H); 576.3 (DHU-analog, M+H) (26% of mixture)

Gly-CUPA: m/e 631.3 (M+H); 633.4 (DHU-analog, M+H) (15% of mixture)

Ala-CUPA: m/e 645.3 (M+H); 647.4 (DHU-analog, M+H) (59% of mixture)

Example 6
Reaction of CUPA with Trimethylsilyl Isocyanate

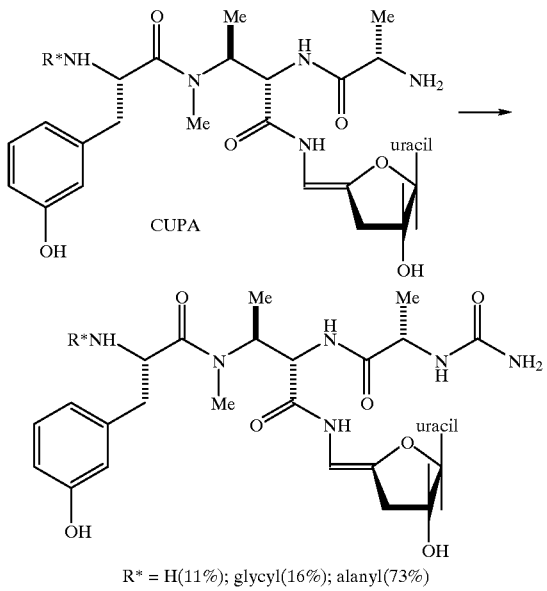

R* = H(11%); glycyl(16%); alanyl(73%)

A solution of trimethylsilyl isocyanate (10 μl of a 1.6 M solution in DMF) was added to CUPA (10 mg) in DMF (750 μl) at 0° C. The solution was stirred at 0° C. for 1 h, then at 20° C. for 12 h. The reaction mixture was then concentrated and further purification by flash chromatography (2 cm³ column, gradient of BuOH:i-PrOH:water—4:2:1 to 3:2:2) to give desired compounds (4 mg) as a white solid: TLC (silica gel, BuOH:i-PrOH:H₂O—4:2:1). Mass spectrum of adducts:

$NH_2$-CUPA-$CONH_2$: m(e 617.1 (M+H), 619.3 (DHU-analog, M+H) (11% of mixture)

Gly-CUPA-$CONH_2$: m/e 674.2 (M+H), 676.2 (DHU-analog, M+H) (16% of mixture)

Ala-CUPA-$CONH_2$: m/e 688.3 (M+H), 690.3 (DHU-analog, M+H) (73% of mixture).

Example 7
Reaction of CUPA with n-Butyl Isocyanate

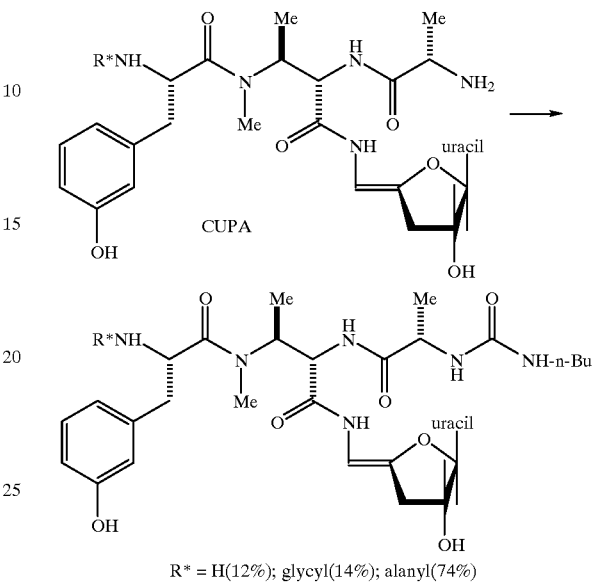

R* = H(12%); glycyl(14%); alanyl(74%)

A solution of n-butyl isocyanate (10 μl of a 0.1M solution in DMF) was added to CUPA (6 mg) in DMF (500 μl) at 0° C. The solution was stirred at 0° C. for 1 h, then at 20° C. for 12 h. The reaction mixture was then concentrated and further purified by chromatography over silica gel (2 cm³ column, BuOH:i-PrOH:water—4:2:1) to give desired compounds (4 mg) as a white solid: TLC (silica gel, BuOH:i-PrOH:H₂O— 4:2: 1) Rf 0.29. Mass spectra:

$NH_2$-CUPA adduct: m/e 673.3 (M+H); 675.4 (DHU-analog, M+H) (12% of mixture)

Gly-CUPA adduct: m/e 730.4 (M+H); 732.4 (DHU-analog, M+H) (14% of mixture)

Ala-CUPA adduct: m/e 744.3 (M+H); 746.4 (DHU-analog, M+H) (74% of mixture).

Example 8
Reaction of CUPA with Methyl (S)-2-Isocyanato-3-phenylpropanoate (Major component is Ala-CUPA-Phe-OH)

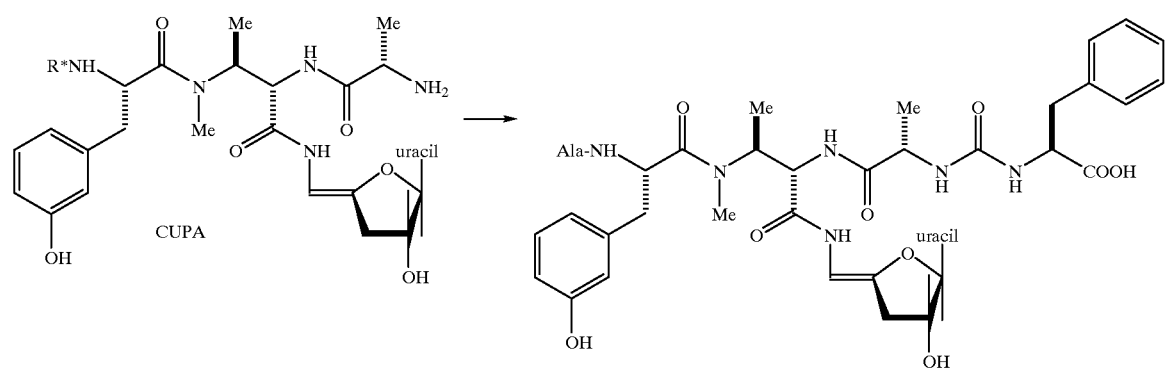

1) A well-stirred cold mixture (0° C.) of phenylalanine methyl ester hydrochloride (200 mg), anhydrous dichloromethane (3 ml), and anhydrous pyridine (295 µl, 4 eq.) was stirred for 15 min. A 2M phosgene solution in toluene (455 µl, 0.98 eq.) was added over 30 sec. followed by stirring for 2 h at 0° C. The reaction mixture was poured into dichloromethane washed with cold 1N hydrochloric acid then ice water. Each aqueous layer was back extracted once with dichloromethane. The combined organic layer was washed once with brine, dried over anhydrous magnesium sulfate and concentrated. Distillation under vacuum afforded methyl (S)-2-isocyanato-3-phenylpropanoate (125 mg).

2) A solution of methyl (S)-2-isocyanato-3-phenylpropanoate (55 µl of a 0.5M solution in dichloromethane) was added to a solution of CUPA (20 mg) in dichloromethane (1.5 ml) at 0° C. The reaction mixture was allowed to warm to room temperature and stirred at that temperature for 12 h. Concentration and chromatography over silica gel (2 cm³ column, gradient BuOH:i-PrOH:water—4:2:1 to 3:2:2) afforded the desired adduct (12.6 mg): TLC (silica gel, BuOH:i-PrOH:H₂O—4:2:1) Rf 0.23.

3) A solution of the above ester (5 mg) in methanol (200 µl) was treated with 0.1M potassium hydroxide (200 µl) at 0° C., and the solution maintained at 0° C. for 16 h. The reaction mixture of diluted with cold water and loaded onto a short column of C₁₈-reverse phase packing. After desalting with 4 ml of water, 1 ml fractions of 30% CH₃CN/water are collected. Fractions 1 and 2 contained the desired compound. Concentration and lyophilization gave desired product (3.5 mg): TLC (C₁₈-reverse phase, 20% CH₃CN/80% 0.1M NH₄OAc pH 7.8 buffer); mass spectrum: Ala-CUPA-Phe-OH, m/e 836.3 (M+H), 838.3 (DHU-analog, M+H).

Example 9
Reaction of CUPA with Ethyl 2-Isocyanatoacetate (Major component is Ala-CUPA-Gly-OH)

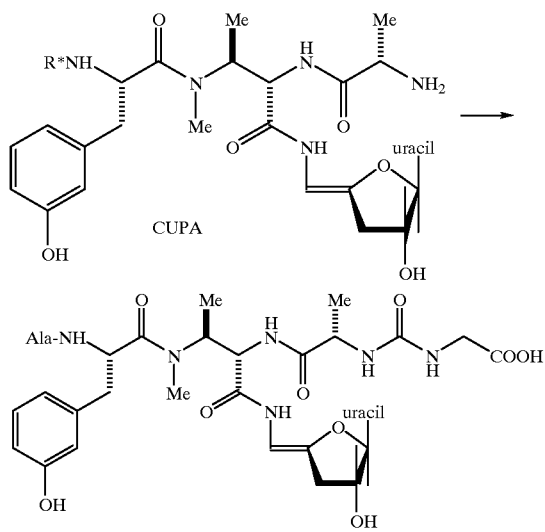

1) To a solution of CUPA (13 mg) in DMF (1 ml) was added ethyl 2-isocyanatoacetate (2 µl) at 0° C. The reaction mixture was stirred at room temperature for 12 h, and then concentrated in vacuo. The residue was chromatographed over silica gel (2 cm³ column, gradient of BuOH:i-PrOH:water—4:2:1 to 3:2:2) to afford the intermediate ester (9 mg): TLC (silica gel, BuOH:i-PrOH:H₂O—4:2:1) Rf 0.18.

2) To a solution of the above ester (3.5 mg), methanol (100 µl), and water (200 µl) was treated with aqueous 0.1N potassium hydroxide (100 µl) at 0° C. The reaction mixture was stirred at 0° C. for 16 h and Dowex-H⁺ resin added. After filtration and concentration in vacuo, the residue was chromatographed (2 cm³ column, BuOH:i-PrOH:water—3:2:2) to afford desired product (1.5 mg): TLC (silica gel, BuOH:i-PrOH:H₂O—4:2:1) Rf 0.48: mass spectrum: Ala-CUPA-Gly-OH, m/e 746.3 (M+H), 748.3 (DHU-analog, M+H).

Although certain embodiments and examples have been used to describe the present invention, it will be apparent to those skilled in the art that the present invention is well adapted to carry out the objects and to obtain the ends and advantages mentioned, as well as those inherent herein and that substitutions and modification to the embodiments and examples shown may be made without detracting from the scope or spirit of the invention.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The specific compounds and methods described herein as presently representative of preferred embodiments are exemplary and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention. For example, those skilled in the art will recognize that the invention may be practiced using a variety of different materials for purification and that a variety of different derivatives can be made.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is not intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Thus, additional embodiments are within the scope of the invention and within the following claims.

What is claimed is:

1. An isolated or purified compound or derivative thereof, wherein said compound is selected from the group consisting of pacidamycin D, pacidamycin-4N, pacidamycin-5N, and pacidamycin-5T.

2. The compound of claim 1, wherein said compound is pacidamycin D or a derivative thereof.

3. The compound of claim 1, wherein said compound is pacidamycin-4N or a derivative thereof.

4. The compound of claim 1, wherein said compound is pacidamycin-5N or a derivative thereof.

5. The compound of claim 1, wherein said compound is pacidamycin-5T or a derivative thereof.

6. A compound consisting of a modified pacidamycin, mureidomycin, or napsamycin uridyl peptide antibiotic, wherein the modification comprises a removal of the carboxy terminal amino acid from said uridyl peptide antibiotic, or a replacement of the carboxy terminal amino acid from said uridyl peptide antibiotic with a different amino acid or a modified amino acid which is optionally linked through a urea linkage.

7. The compound of claim 6, wherein said uridyl peptide antibiotic compound is selected from the groups consisting of a derivative of a naturally occurring pacidamycin compound, a derivative of a naturally occurring mureidomycin compound, and a derivative of a naturally occurring napsamycin compound.

8. The compound of claim 6, wherein said compound has antibacterial or antifungal activity.

9. The compound of claim 6, wherein said compound is prepared by a replacement of the carboxy terminal amino acid from said compound with a different amino acid or a modified amino acid which is linked through a urea linkage.

10. A pharmaceutical composition, comprising a pharmaceutically acceptable carrier or excipient and a uridyl peptide antibiotic compound or a derivative thereof, wherein said compound is selected from the group consisting of pacidamycin D, pacidamycin-4N, pacidamycin-5N, pacidamycin-5T, wherein said compound results from a removal of the carboxy terminal amino acid from said uridyl peptide antibiotic, or a replacement of the carboxy terminal amino acid from said uridyl peptide antibiotic with a different amino acid or a modified amino acid which is optionally linked through a urea linkage.

11. The pharmaceutical composition of claim 10, wherein said compound is pacidamycin D or a derivative thereof.

12. The pharmaceutical composition of claim 10, wherein said compound is pacidamycin-4N or a derivative thereof.

13. The pharmaceutical composition of claim 10, wherein said compound is pacidamycin 5N or a derivative thereof.

14. The pharmaceutical composition of claim 10, wherein said compound is pacidamycin-5T or a derivative thereof.

15. The pharmaceutical composition of claim 10, wherein said compound is a CUPA compound or a derivative thereof.

* * * * *